United States Patent [19]
Kriesel et al.

[11] Patent Number: 5,779,676
[45] Date of Patent: Jul. 14, 1998

[54] FLUID DELIVERY DEVICE WITH BOLUS INJECTION SITE

[75] Inventors: Marshall S. Kriesel, St. Paul; Farhad Kazemzadeh, Bloomington; Matthew B. Kriesel, St. Paul, all of Minn.; William W. Feng, Lafayette, Calif.; Steve C. Barber, Shorewood, Minn.; William J. Kluck, Hudson, Wis.

[73] Assignee: Science Incorporated, Bloomington, Minn.

[21] Appl. No.: 606,090

[22] Filed: Feb. 23, 1996

Related U.S. Application Data

[63] Continuation-in-part of Ser. No. 541,184, Oct. 11, 1995.
[51] Int. Cl.$^6$ .................................................... A61M 37/00
[52] U.S. Cl. ........................... 604/132; 604/83; 604/890.1
[58] Field of Search .............................. 604/82, 83, 85, 604/131, 132, 151, 153, 890.1; 128/DIG. 12

[56] References Cited

U.S. PATENT DOCUMENTS

| | | | |
|---|---|---|---|
| 4,193,397 | 3/1980 | Tucker et al. | 604/83 X |
| 4,474,575 | 10/1984 | Eckenhoff et al. | 604/131 |
| 4,668,231 | 5/1987 | DeVries et al. | 604/891 |
| 4,968,301 | 11/1990 | DiPalma et al. | 604/132 |
| 4,969,873 | 11/1990 | Steinbach et al. | 604/93 |

*Primary Examiner*—Corrine M. McDermott
*Attorney, Agent, or Firm*—James E. Brunton

[57] ABSTRACT

An apparatus for accurately infusing fluids into a patient at specific rates over an extended period of time. The apparatus is of a low profile, laminate or layered construction having a stored energy source in the form of a distendable membrane, which in cooperation with the base of the apparatus, defines one or more fluid reservoirs, each having a fluid inlet and a fluid outlet. The apparatus further includes, a novel, conformable ullage made of yieldable materials which uniquely conform to the shape of the elastomeric membrane as the membrane returns to its less distended configuration. This arrangement will satisfy even the most stringent medicament delivery tolerance requirements and will elegantly overcome the limitations of materials selection encountered in devices embodying solely a rigid ullage construction. Additionally, in one form of the invention, the apparatus includes a novel fill assembly for controllably filling the reservoirs of the device in the field.

25 Claims, 18 Drawing Sheets

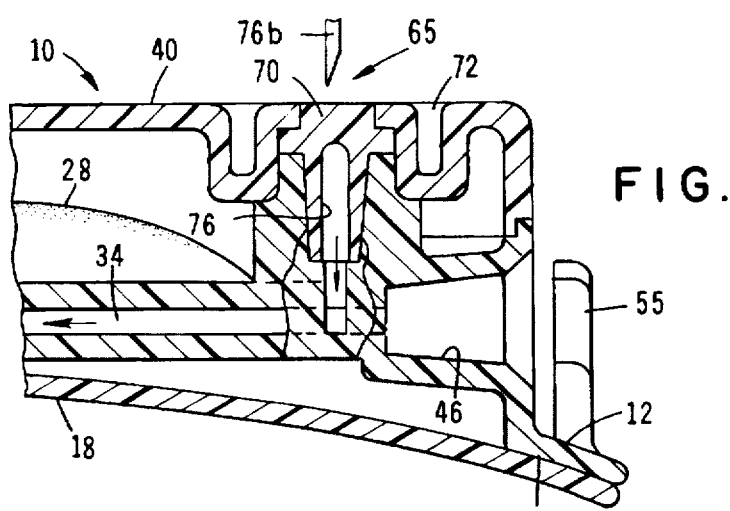
FIG. 6
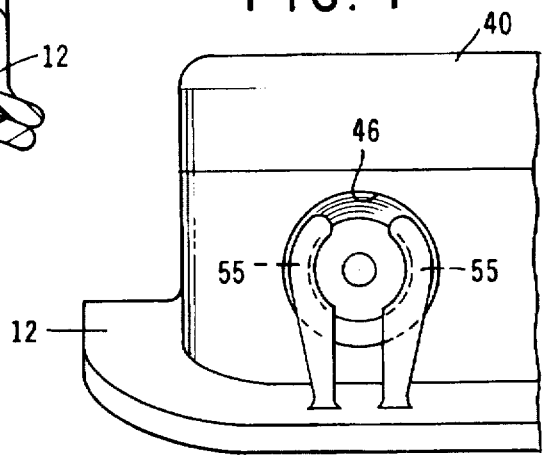
FIG. 7
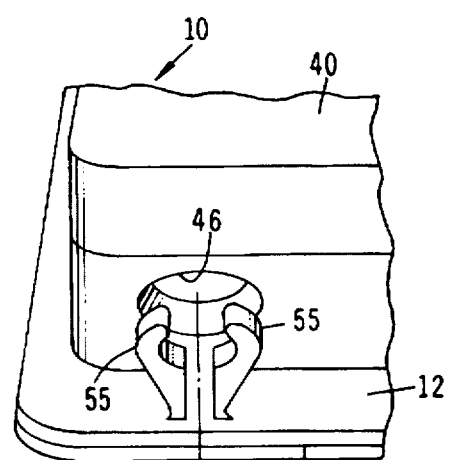
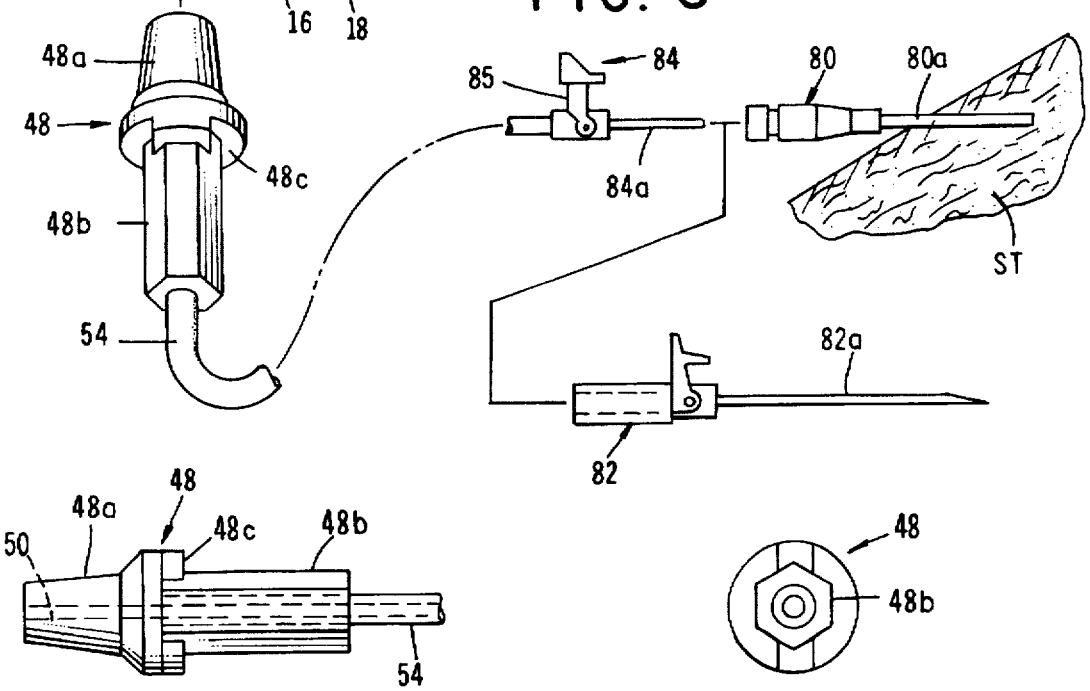
FIG. 8
FIG. 9
FIG. 9A

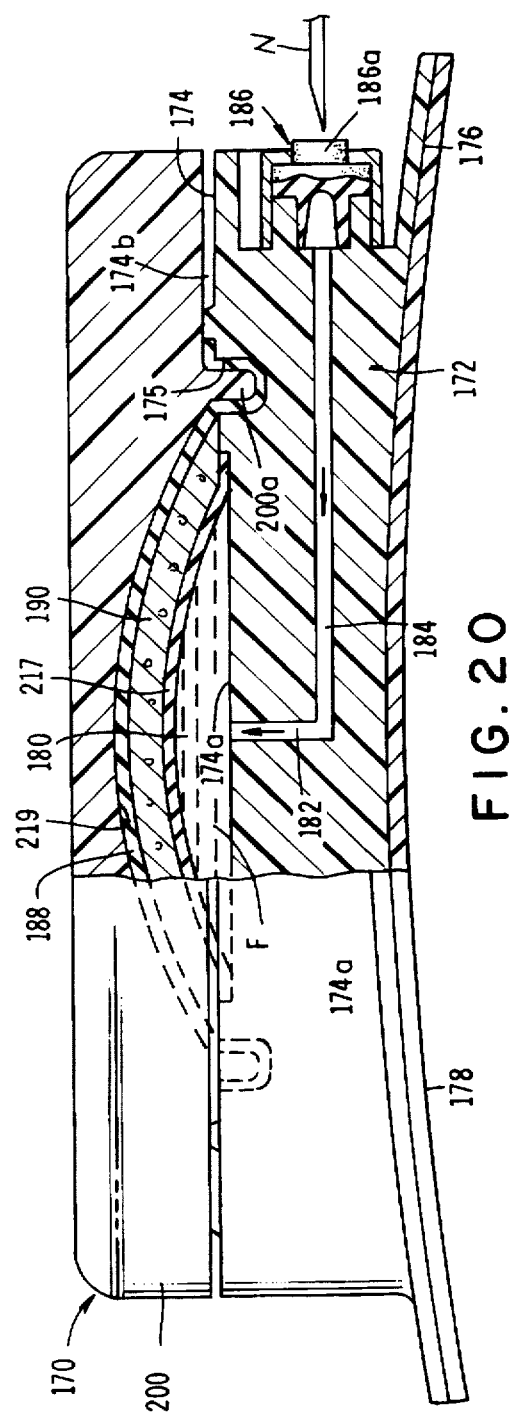
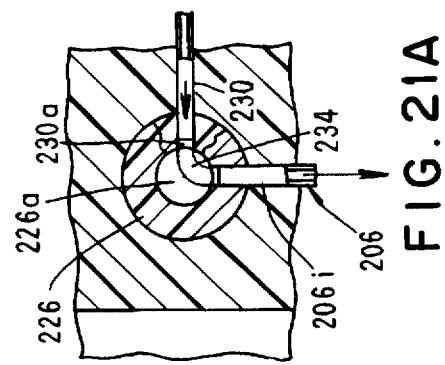
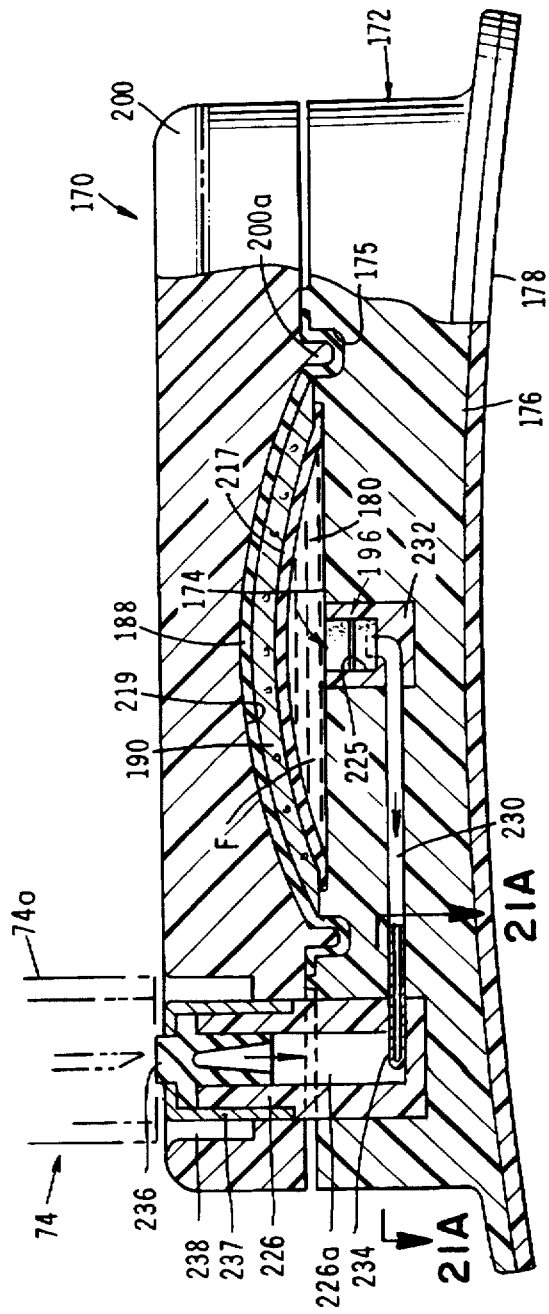
FIG. 20
FIG. 21A
FIG. 21

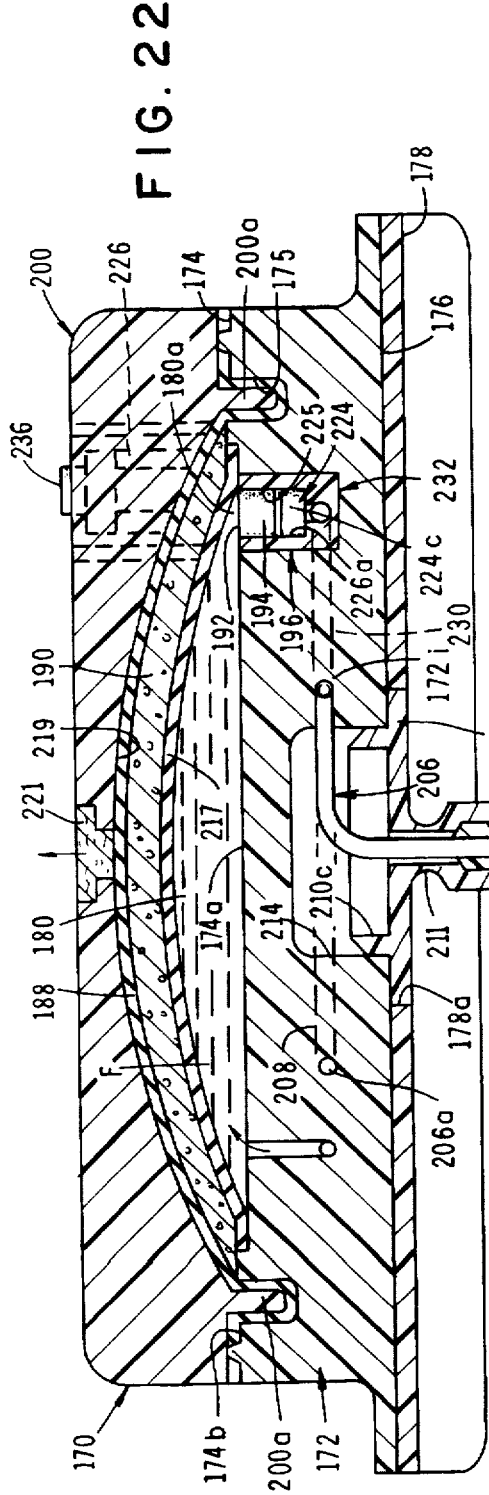
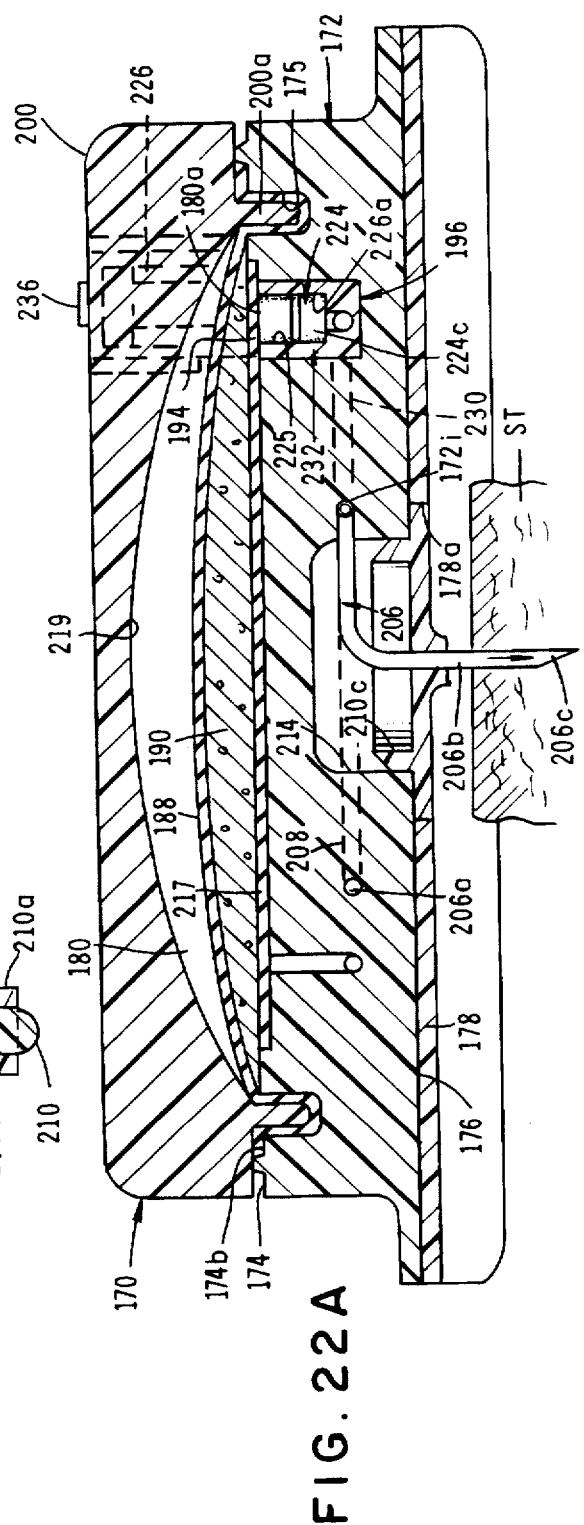

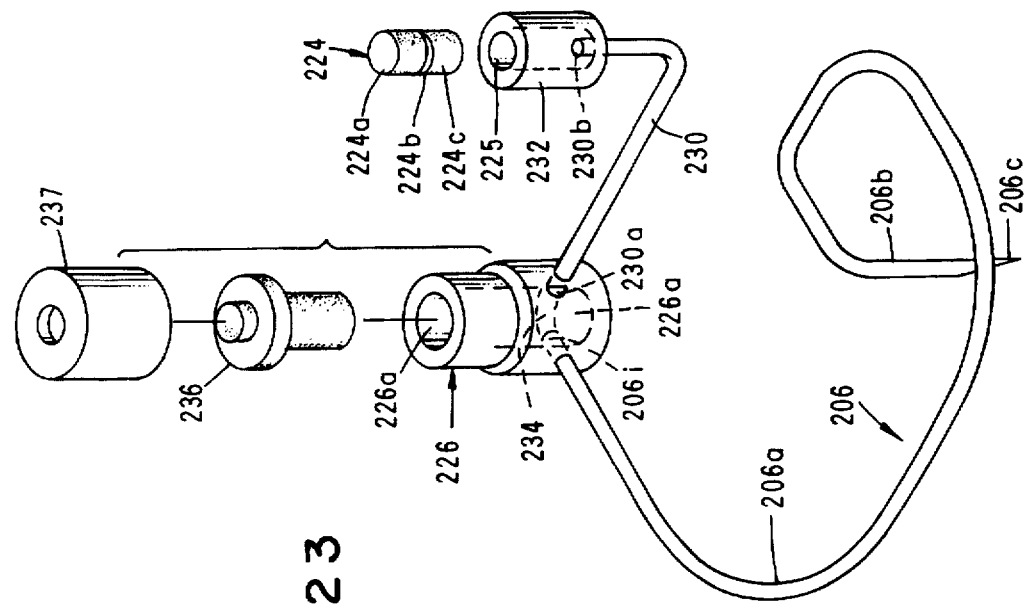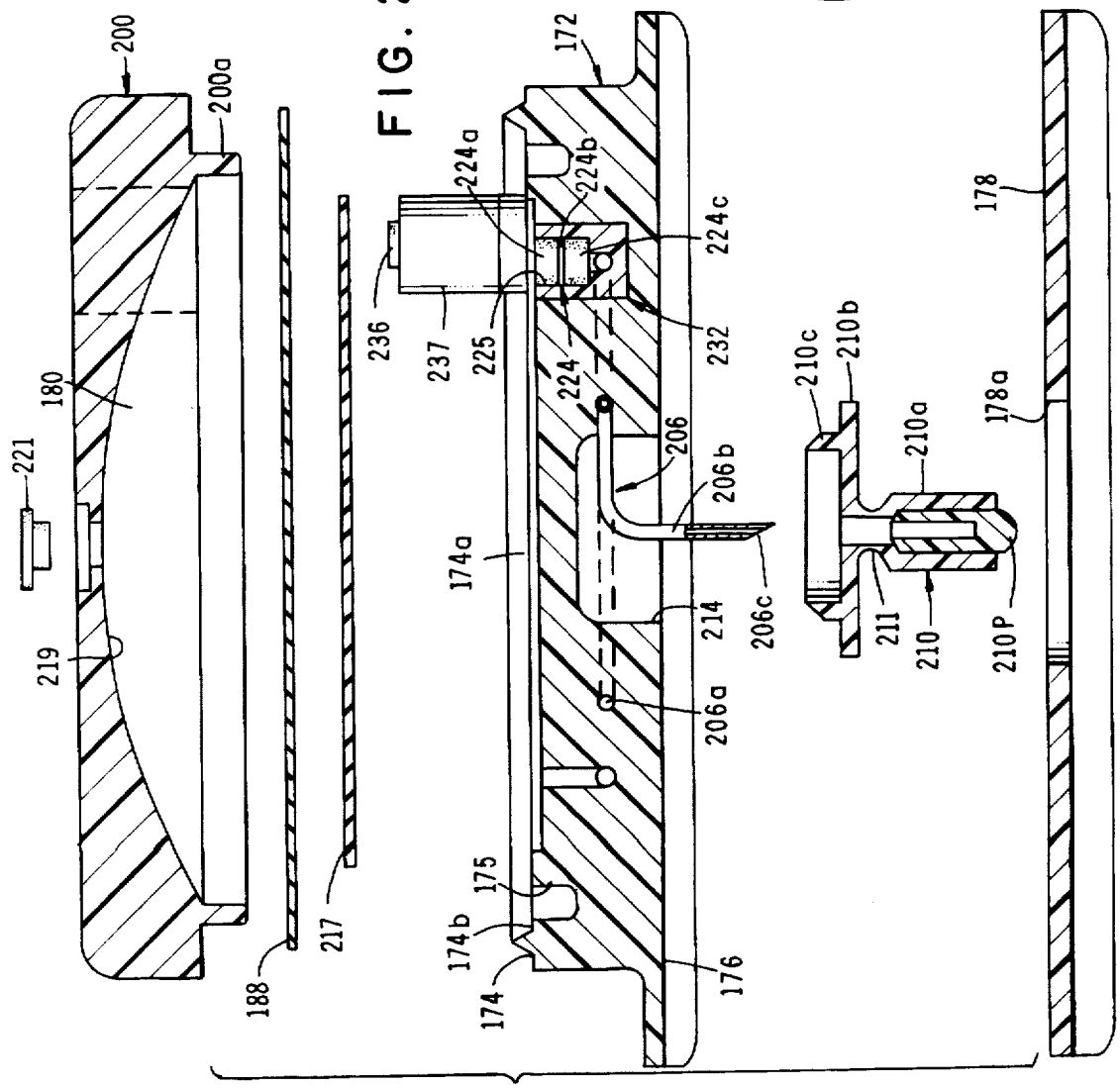

WHERE R-1 ≠ R-2

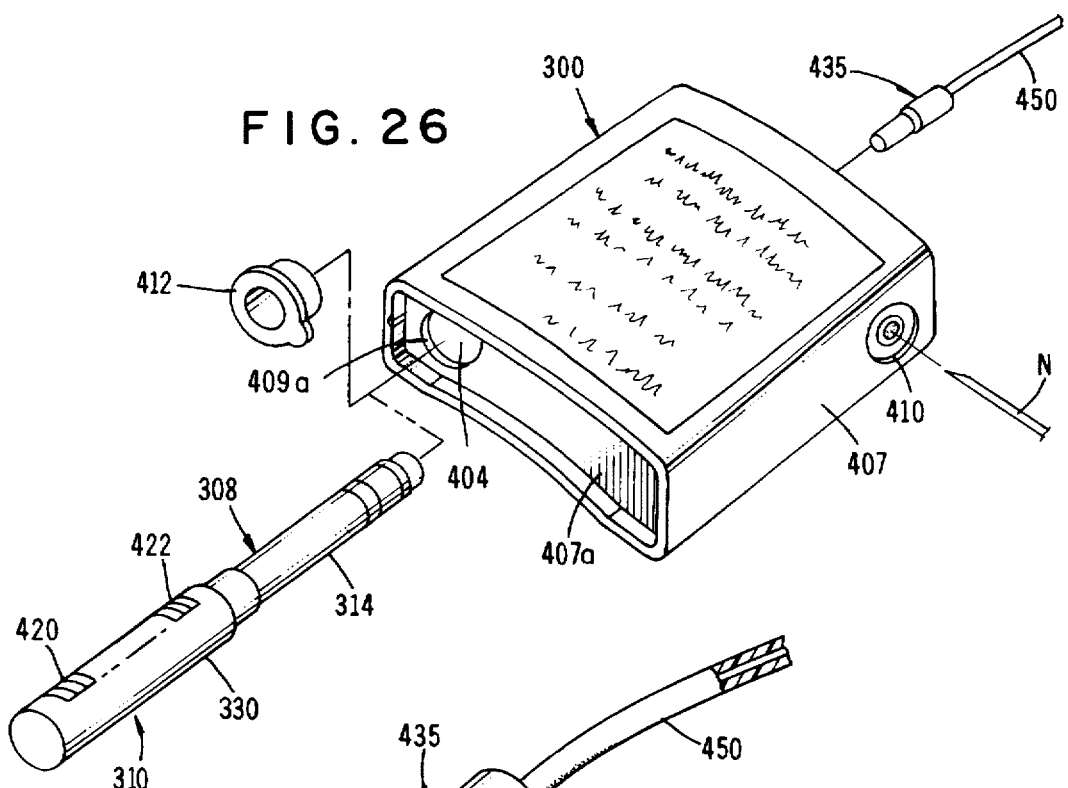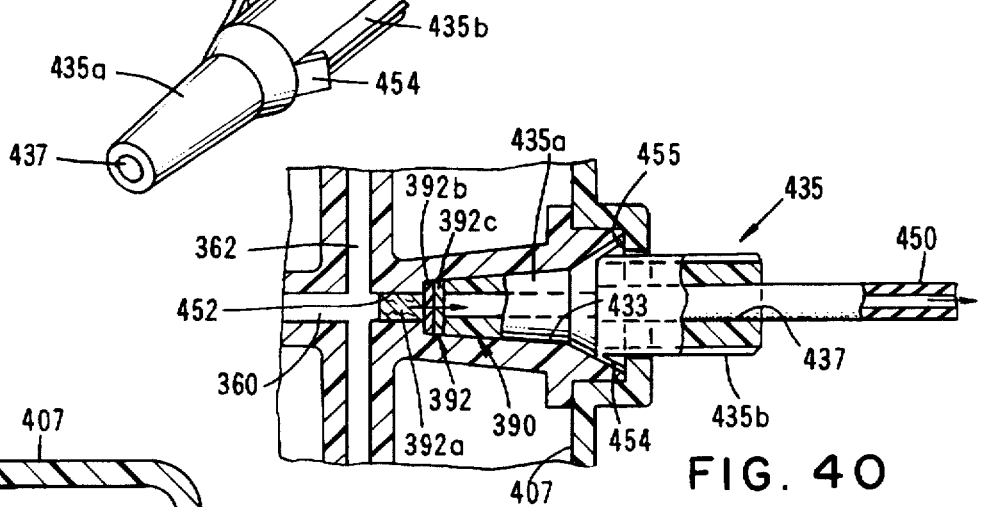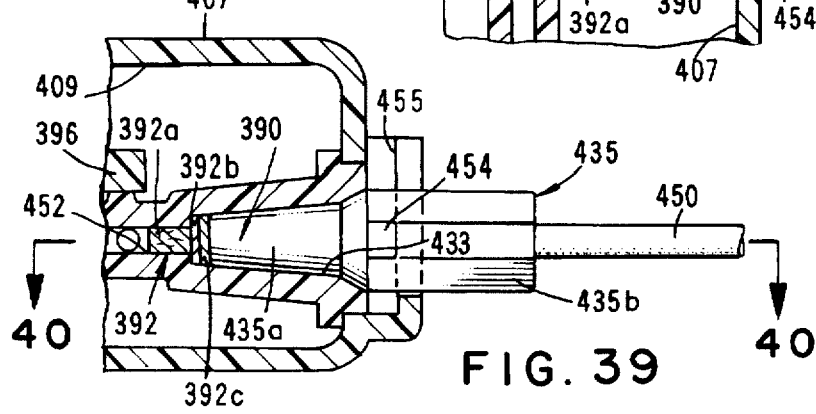

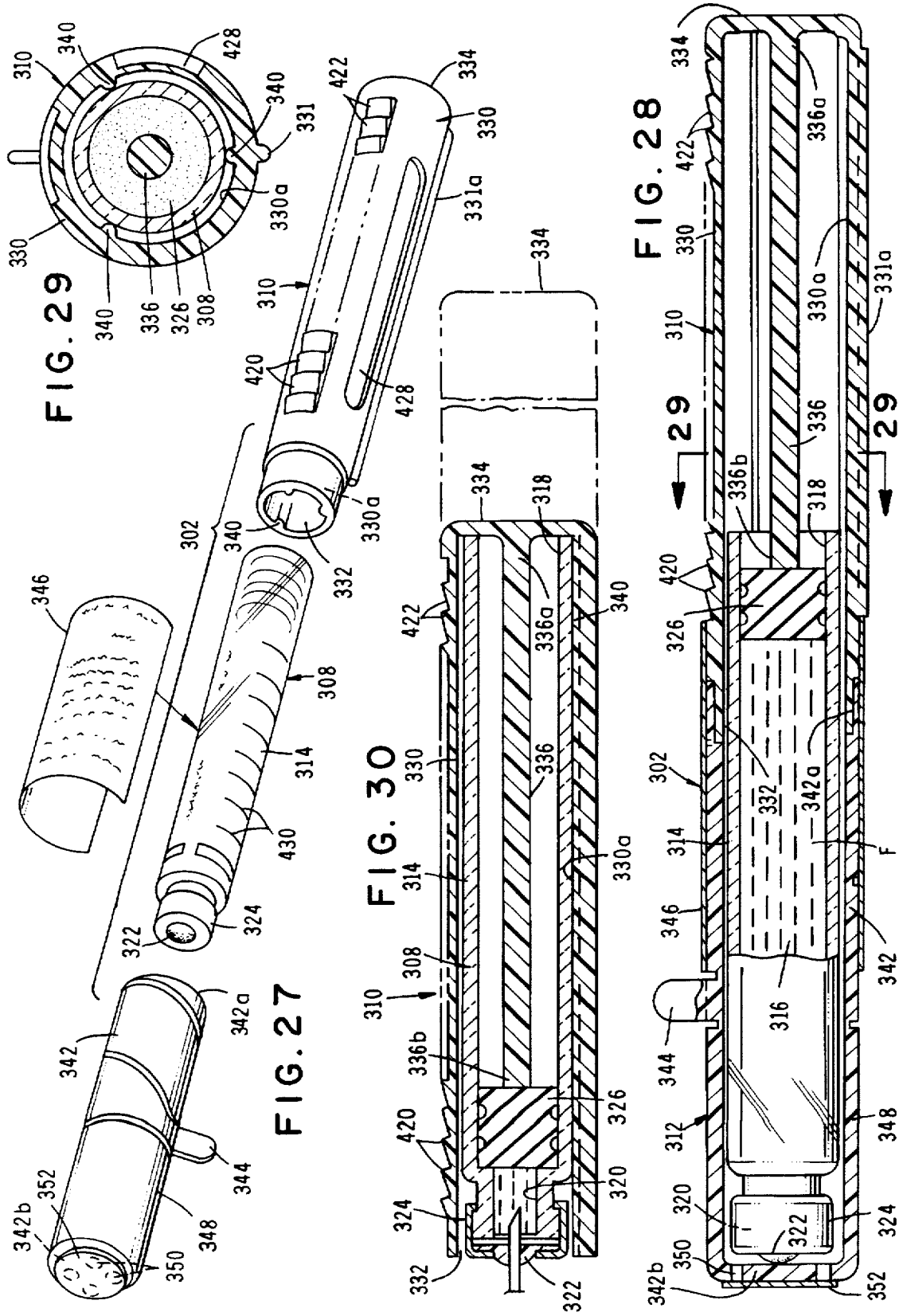

FLUID DELIVERY DEVICE WITH BOLUS INJECTION SITE

This is a Continuation-In-Part application of U.S. Ser. No. 08/541,184, pending filed Oct. 11, 1995.

BACKGROUND OF THE INVENTION

1. Field of the Invention

The present invention relates generally to fluid delivery devices. More particularly, the invention concerns an improved fluid delivery apparatus for precise delivery over time of medicinal liquids to an ambulatory patient, the device including a bolus injection site for bolus delivery of medicinal liquids as from time to time may be required.

2. Discussion of the Invention

A number of different types of liquid dispensers for dispensing medicaments to ambulatory patients have been suggested. Many of the devices seek either to improve or to replace the traditional hypodermic syringe which has been the standard for delivery of liquid medicaments such as insulin solution.

Those patients that require frequent injections of the same or different amounts of medicament, find the use of the hypodermic syringe both inconvenient and unpleasant. Further, for each injection, it is necessary to first draw the injection dose into the syringe, then check the dose and, after making certain that all air has been expelled from the syringe, finally, inject the dose. This cumbersome and tedious procedure creates an unacceptable probability of debilitating complications, particularly for the elderly and the infirm.

One example of the urgent need for an improved liquid delivery device for ambulatory patients can be found in the stringent therapeutic regimens used by insulin-dependent diabetics. The therapeutic objective for diabetics is to consistently maintain blood glucose levels within a normal range much as the normally functioning pancreas would do by secreting a very low level of extremely fast-acting insulin at a basal rate into the blood stream throughout the day and night.

Consider the normal individual who doesn't have diabetes. A normal individual's cells require energy throughout the day just to maintain a basal metabolic rate. This energy is supplied to the cells by glucose that is transported from the bloodstream to the cells by insulin. When food is consumed, the blood glucose level rises and the pancreas responds by releasing a surge of fast-acting insulin. To mimic this natural process with individual injections, the individual would have to administer minuscule amounts of fast-acting insulin every few minutes throughout the day and night.

Conventional therapy usually involves injecting, separately, or in combination, fast-acting and slower-acting insulin by syringe several times a day, often coinciding with meals. The dose must be calculated based on glucose levels present in the blood. Slower-acting insulin is usually administered in the morning and evening to take advantage of longer periods of lower level glucose uptake. Fast-acting insulin is usually injected prior to meals. If the dosage of fast-acting insulin is off, the bolus administered may lead to acute levels of either glucose or insulin resulting in complications, including unconsciousness or coma. Over time, high concentrations of glucose in the blood can also lead to a variety of chronic health problems, such as vision loss, kidney failure, heart disease, nerve damage, and amputations.

A recently completed study sponsored by the National Institutes of Health (NIH) investigated the effects of different therapeutic regimens on the health outcomes of insulin-dependent diabetics. This study revealed some distinct advantages in the adoption of certain therapeutic regimens. Intensive therapy that involved intensive blood glucose monitoring and more frequent administration of insulin by conventional means, for example, syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin by means of a convenient and reliable delivery device over an extended period of time represents one means of improving insulin management. Basal rate delivery involves the delivery of very small volumes of fluid (for example, 0.3–3 mL, depending on body mass) over comparatively long periods of time (18–24 hours). As will be appreciated from the discussion which follows, the apparatus of the present invention is uniquely suited to provide precise fluid delivery management at a low cost in those cases where a variety of precise dosage schemes are of utmost importance.

An additional important feature of the apparatus of the present invention is the provision of a bolus injection site which permits, in addition to the basal rate, a bolus delivery of medication on an as-needed basis. For example, if the apparatus is being used for basal delivery of insulin over an extended period of time, should a bolus delivery of medication be required to manage an anticipated increase in blood sugar, such a bolus delivery can be quickly and easily accomplished using the device's bolus injection site and eliminates the need for a direct subdermal injection at an alternate site on the individual's body.

With regard to the prior art, one of the most versatile and unique fluid delivery apparatus developed in recent years is that developed by one of the present inventors and described in U.S. Pat. No. 5,205,820. The component of this novel fluid delivery apparatus generally include: a base assembly, an elastomeric membrane serving as a stored energy means, fluid flow channels for filling and delivery, flow control means, a cover, and an ullage which comprises a part of the base assembly. The ullage in these devices is provided in the form of a semi-rigid structure having flow channels leading from the top of the structure through the base to inlet or outlet ports of the device. Since the inventions described herein represent improvements over those described in U.S. Pat. No. 5,205,820, this patent is hereby incorporated by reference as though fully set forth herein.

In the rigid ullage configuration described in U.S. Pat. No. 5,205,820, the stored energy means of the device must be superimposed over the ullage to form the fluid-containing reservoir from which fluids are expelled at a controlled rate by the elastomeric membrane of the stored energy means tending to return to a less distended configuration in the direction toward the ullage. With these constructions, the stored energy membrane is typically used at higher extensions over a significantly large portion of the pressure-deformation curve.

For good performance, the elastomeric membrane materials selected for construction of the stored energy membrane must have good memory characteristics under conditions of extension; low stress relaxation; good resistance to chemical and radiological degradation; and appropriate gas permeation characteristics depending upon the end application to be made of the device. Once an elastomeric membrane material is chosen that will optimally meet the desired performance requirements, there still remain certain limitations to the level of refinement of the delivery tolerances that can be achieved using the rigid ullage configuration. These result primarily from the inability of the rigid ullage to conform to the changing geometry of the elastomeric membrane near the end of the delivery period. This nonconformity can lead to extended delivery rate tail-off and higher residual problems when extremely accurate delivery is required. For example, when larger volumes of fluid are to be delivered, the tail-off volume represents a smaller portion of the fluid amount delivered and therefore exhibits must less effect on the total fluid delivery profile, but in very small dosages, the tail-off volume becomes a larger portion of the total volume. This sometimes places severe physical limits on the range of delivery profiles that may easily be accommodated using the rigid ullage configuration. An additional penalty inherent in rigid ullage construction is the high Z axis height of the ullage that will be required to maintain acceptable flow tail off delivery requirements.

As will be better appreciated from the discussion which follows, the apparatus of the present invention provides a unique and novel improvement for a disposable dispenser of simple but highly reliable construction that may be adapted to many applications of use. A particularly important aspect of the improved apparatus is the incorporation of conformable ullages made of yieldable materials which uniquely conform to the continuously changing geometry of the stored energy membrane during the delivery cycle. This novel construction will satisfy even the most stringent delivery tolerance requirements and elegantly overcomes the limitation of materials selection.

Another useful liquid delivery device is that described in U.S. Pat. No. 5,226,896 issued to Harris. This device comprises a multidose syringe having the same general appearance as a pen or mechanical pencil, the device is specifically adapted to provide for multiple measured injections of materials such as insulin or human growth hormones.

Still another type of liquid delivery device is disclosed in U.S. Pat. No. 4,592,745 issued to Rex et al. This device is, in principle, constructed as a hypodermic syringe, but differs in that it enables dispensing of a predetermined portion from the available medicine and in that it dispenses very accurate doses.

The present invention seeks to significantly improve over the prior art by providing a novel fluid delivery device having one or more fluid reservoirs, which is low in profile, is compact, is easy to use by ambulatory patients, and is eminently capable of meeting the most stringent of fluid delivery tolerance requirements. Additionally, the device provides novel means for accomplishing immediate bolus delivery of medication on an as-needed basis.

SUMMARY OF THE INVENTION

It is an object of the present invention to provide an apparatus having a self-contained stored energy membrane for expelling fluids at a precisely controlled rate which is of a compact, extremely low profile, laminate construction. More particularly, it is an object of the invention to provide such an apparatus which is of very low profile so that it can conveniently be used for the precise delivery of pharmaceutical fluids, such as insulin solution and the like, into an ambulatory patient at controlled rates over extended periods of time.

It is another object of the invention to provide an apparatus of the aforementioned character which is highly reliable and easy-to-use by lay persons in a non-hospital environment.

It is another object of the invention to provide an apparatus as described in the preceding paragraphs which, can be used for both basal and bolus delivery of fluids. In this regard, the apparatus includes a novel and unique bolus injection site which can be used to deliver bolus doses of medication as may be required.

Another object of the invention is to provide an apparatus which embodies a conformable mass which defines an ullage within the reservoir of the device which will closely conform to the shape of the stored energy membrane thereby effectively avoiding extended flow delivery rate tail-off at the end of the fluid delivery period and thus precisely controls the time of delivery.

A further object of the invention is to provide a low profile, fluid delivery device of laminate construction which can meet even the most stringent basal fluid delivery tolerance requirements and at the same time permit bolus delivery of medicaments to the patient as may be required.

Another object of the invention is to provide an apparatus of the character described which, due to its unique construction, can be manufactured inexpensively in large volume by automated machinery.

Other objects of the invention are set forth in U.S. Pat. No. 5,205,820 which is incorporated herein by reference and still further objects will become apparent from the discussion which follows.

BRIEF DESCRIPTION OF THE DRAWINGS

FIG. 4 is an enlarged cross-sectional view taken along lines 4—4 of FIG. 2.

FIG. 5 is a greatly enlarged, cross-sectional view taken along lines 5—5 of FIG. 2.

FIG. 6 is an enlarged, cross-sectional view taken along lines 6—6 of FIG. 2.

FIG. 7 is a greatly enlarged, fragmentary view of the liquid delivery port of the device and of the locking tabs for lockably interconnecting a quick connect delivery fitting with the base of the device.

FIG. 8 is a generally perspective, exploded, view of the liquid delivery port of the device and of an infusion set usable with the device.

FIG. 9 is a cross-sectional view of the quick connect delivery fitting shown in FIG. 8.

FIG. 9A is an end view of the quick connect fitting shown in FIG. 9.

FIG. 20 is a cross-sectional view taken along lines 20—20 of FIG. 19.

FIG. 21 is a cross-sectional view taken along lines 21—21 of FIG. 19.

FIG. 21A is a fragmentary, cross-sectional view taken along lines 21A—21A of FIG. 21.

FIG. 22 is a cross-sectional view taken along lines 22—22 of FIG. 19.

FIG. 22A is a cross-sectional view similar to FIG. 22 but showing the fluid being expelled from the fluid reservoir into the body subdermal tissue.

FIG. 23 is a cross-sectional, exploded view of this latest embodiment of the invention.

FIG. 24 is an enlarged, generally perspective, exploded view of the bolus injection port of the device.

FIG. 26 is a generally perspective, exploded view of an alternate embodiment of the liquid delivery device of the present invention showing a dispensing and a fill assembly usable for filling the fluid reservoir of the dispensing assembly.

FIG. 27 is a generally perspective, exploded view of one form of the fill assembly of the present invention.

FIG. 28 is an enlarged cross-sectional view of the fill assembly illustrated in FIG. 27 as it appears in the assembled configuration.

FIG. 29 is an enlarged, cross-sectional view taken along lines 29—29 of FIG. 28.

FIG. 30 is a cross-sectional view similar to FIG. 28, but showing the appearance of the component parts of the fill assembly after the plunger of the container has been telescopically moved from a first to a second position.

FIG. 39 is a greatly enlarged, fragmentary view of the liquid delivery port of the device and of the quick connect delivery fitting which is interconnectable with the base of the device.

FIG. 40 is a cross-sectional view taken along lines 40—40 of FIG. 39.

FIG. 41 is an enlarged, generally perspective view of the quick connect delivery fitting showing the locking tabs for lockably interconnecting the fitting with the base of the device.

DESCRIPTION OF THE INVENTION

Figure 1:
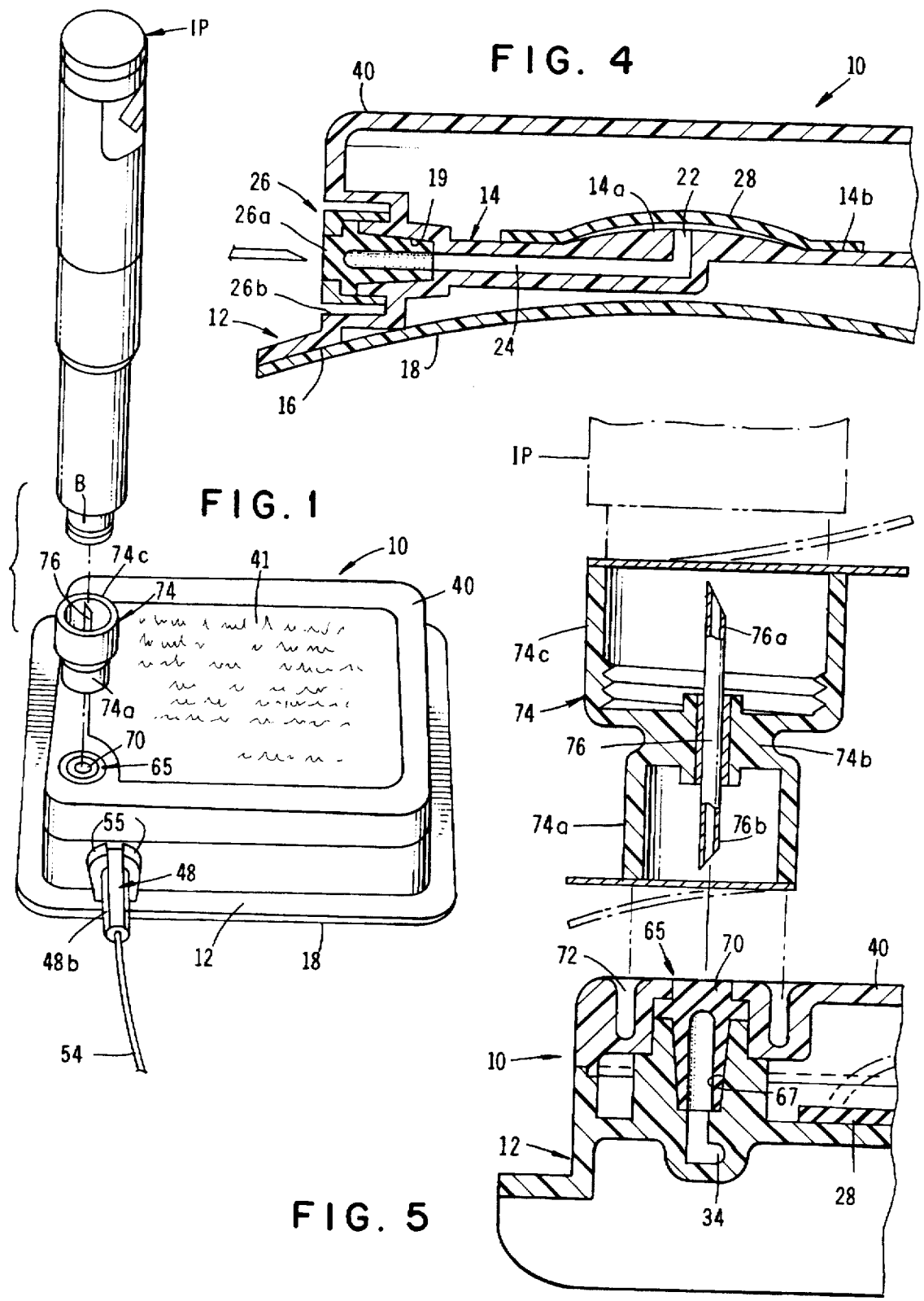
FIG. 1 is a generally perspective, exploded view of one embodiment of the liquid delivery device of the present invention showing an ancillary syringe type device usable for bolus delivery of liquid medication via the bolus injection site of the device.

Referring to the drawings and particularly to FIGS. 1 through 10, one form of the low profile fluid delivery device of the invention is there shown and generally designated by the numeral 10. The device comprises a base 12, having an upper surface 14 including a central convex portion 14a and a peripheral portion 14b circumscribing central portion 14a. As best seen in FIGS. 1 and 4, base 12 is also provided with a lower surface 16 to which a patient interconnection means or adhesive pad assembly 18 is connected. In a manner presently to be described, pad assembly 18 functions to releasably interconnect the device to the patient so as to hold it securely in place during the liquid delivery step.

Figure 2:
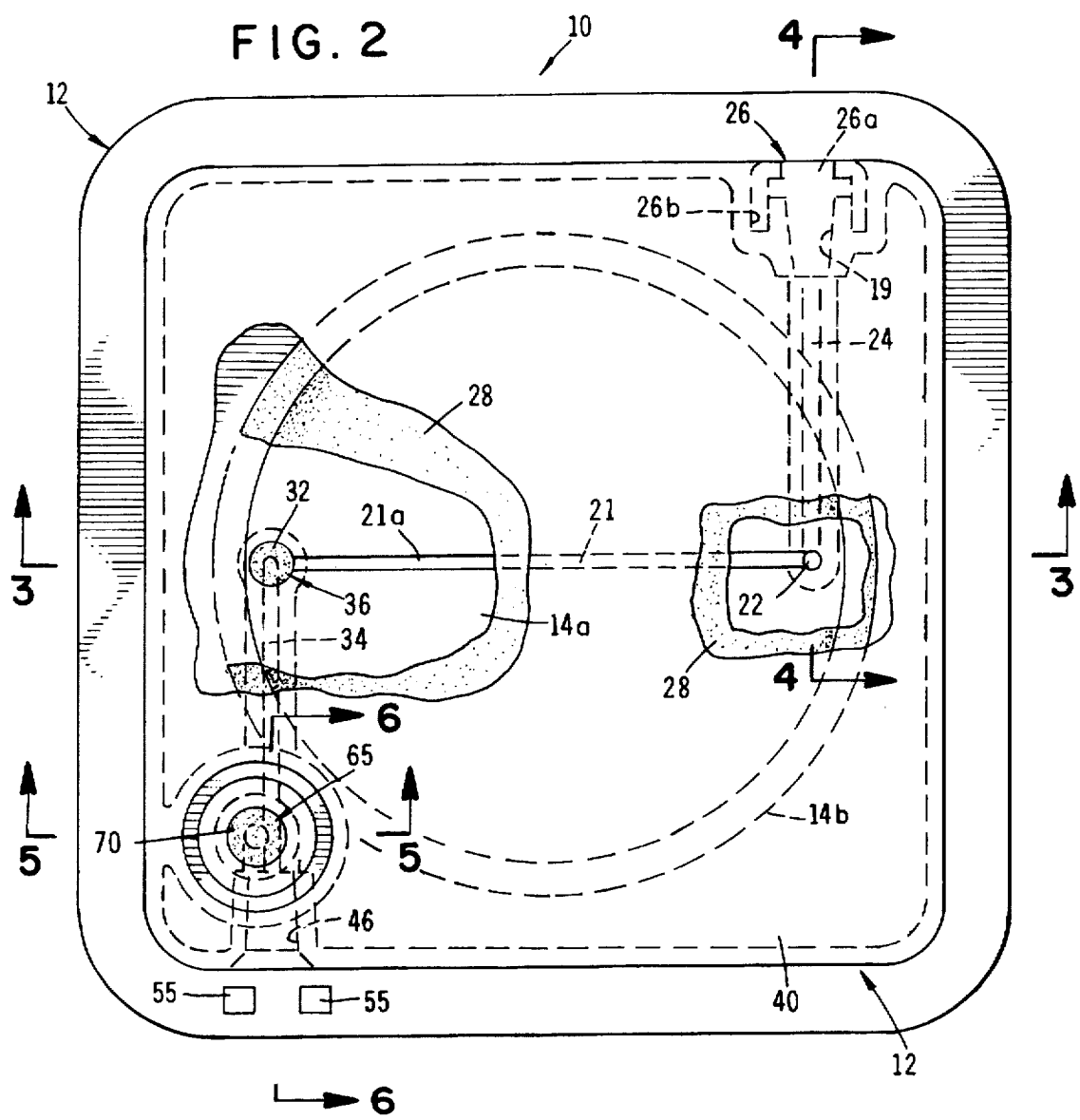
FIG. 2 is a top plan view of the invention shown in FIG. 1 partly broken away to show internal construction.
Figure 3:
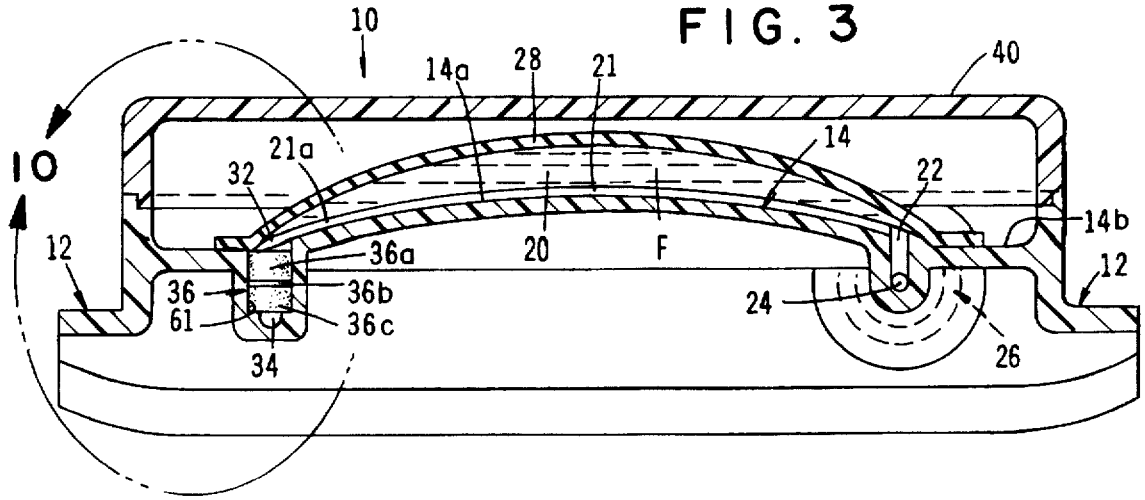
FIG. 3 is a cross-sectional view taken along lines 3—3 FIG. 2.

A stored energy means cooperates with the upper surface 14 of base 12 to form a reservoir 20 having an inlet port 22 which is in communication with a flow passageway 24 which, in turn, communicates with a filling means shown here as a septum assembly 26 (FIGS. 2, 3, and 4). The stored energy means is here provided in the form of at least one distendable membrane 28 which is superimposed over base 12. Membrane 28 is distendable as a result of pressure imparted on the membrane by fluids "F" introduced into reservoir 20 through inlet port 22 (FIGS. 2 and 3). As membrane 28 is distended in the manner shown in FIG. 3, internal stresses will be established, which stresses tend to move the membrane toward a less distended configuration and in a direction toward base 12. Membrane 28 can be constructed from a single membrane or from multiple membranes to form a laminate construction of the character shown in FIG. 39 of U.S. Pat. No. 5,279,558, which patent is incorporated herein by reference. Membrane 39 can be formed from a variety of elastomers of the character discussed in detail in U.S. Pat. No. 5,279,558 (see columns 9 and 10 of the patent).

Provided within the reservoir portion of the device, which includes fluid reservoir 20 and the convex central portion of the base, is ullage defining means for providing ullage within the reservoir and for engagement with membrane 28 as the membrane moves toward its less distended starting configuration in the manner shown in FIG. 4. The ullage defining means in the embodiment of the invention shown in FIGS. 1 through 10 comprises the convex central portion 14a of base 12 and defines an engagement surface for engagement by the distendable membrane as the membrane returns to its less distended configuration. As the membrane returns toward this less distended configuration, fluid contained within the reservoir 20 will flow through a fluid passageway 21a formed in the convex central portion 21, the base, and thence uniformly outwardly of the reservoir through an outlet port 32. The fluid will then flow into a fluid outlet passageway 34 via flow control means, the character of which will presently be described.

Superimposed over base 12 is a cover 40 which functions to sealably enclose membrane 28. A medicament and use label 41 is affixed to cover 40 in the manner shown in FIG. 1. Base 12 and cover 40 can be constructed from a number of different materials of the character described in U.S. Pat. No. 5,279,558 (see columns 9 and 11).

Referring particularly to FIGS. 1, 6, 8, and 9 in the present form of the invention, the infusion means for infusing medicinal fluids from reservoir 20 into the patient comprises a tapered outlet cavity 46 formed in base 12 (FIG. 6) which sealably receives a quick connect delivery fitting 48 that comprises a part of the infusion means of the invention. Fitting 48 includes a tapered inboard end portion 48a and a hexagonally shaped body portion 48b. A central bore 50 extends through portions 48a and 48b and communicates at its outboard end with a cannula 54 which also forms a part of the infusion means of the invention for infusing liquids into the patient. The inboard end of bore 50 communicates with fluid passageway 34 when fitting 48 is seated within cavity 46 in the manner shown in FIG. 1.

In order to releasably lock quick connect delivery fitting 48 in the fluid delivery position within cavity 46 and in fluid communication with passageway 34, locking means shown here as resiliently deformable locking tabs 55 are provided on base 12 (FIG. 7). Upon pushing inwardly on fitting 48, tabs 55 will separate so that tapered portion 48a of the fitting can be introduced into cavity 46. As the fitting seats within portion 46, the resiliently deformable locking tabs will close about portion 48b and will engage shoulder 48c in the manner to lockably interconnect the infusion means with the base.

Filling reservoir 20 is accomplished by introducing fluid into the reservoir under pressure via fill means which here comprises a septum assembly 26 mounted in base 12 (FIG. 4). Septum assembly 26 is of a similar construction to the bolus injection site of the invention, the nature of which will presently be described. More particularly, the septum assembly includes a pierceable septum 26a which is mounted within a tapered cavity 19 formed in base 12. Surrounding septum 26a is a generally circularly shaped guide channel 26b. Using a conventional syringe assembly, fluid can be introduced into passageway 24 via a pierceable septum 26a which comprises a part of septum assembly 26. During this filling step, distendable membrane 28 is distended outwardly in the manner shown in FIGS. 3 and 10 and internal stresses are thereby formed in the membrane which tend to urge it toward its less distended starting configuration. In a manner presently to be described, a mechanical injection pen can also be used to fill the fluid reservoir.

Figure 10:
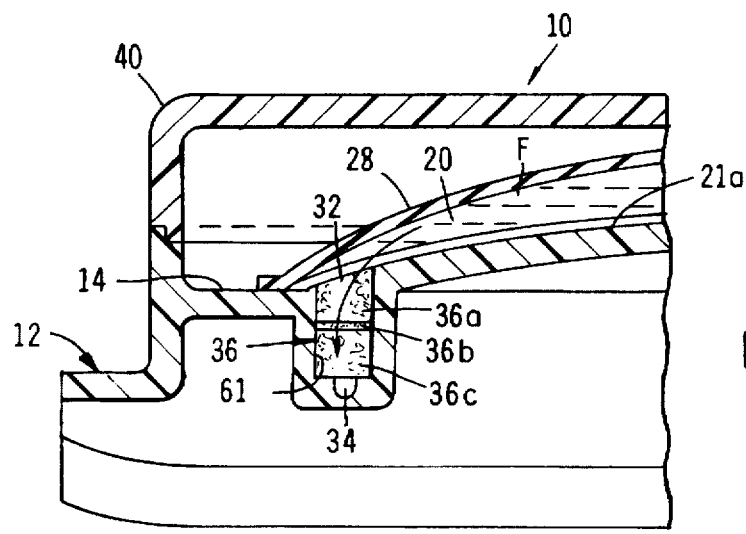
FIG. 10 is a greatly enlarged cross-sectional view of the area designated as 10 in FIG. 3.
Figure 11:
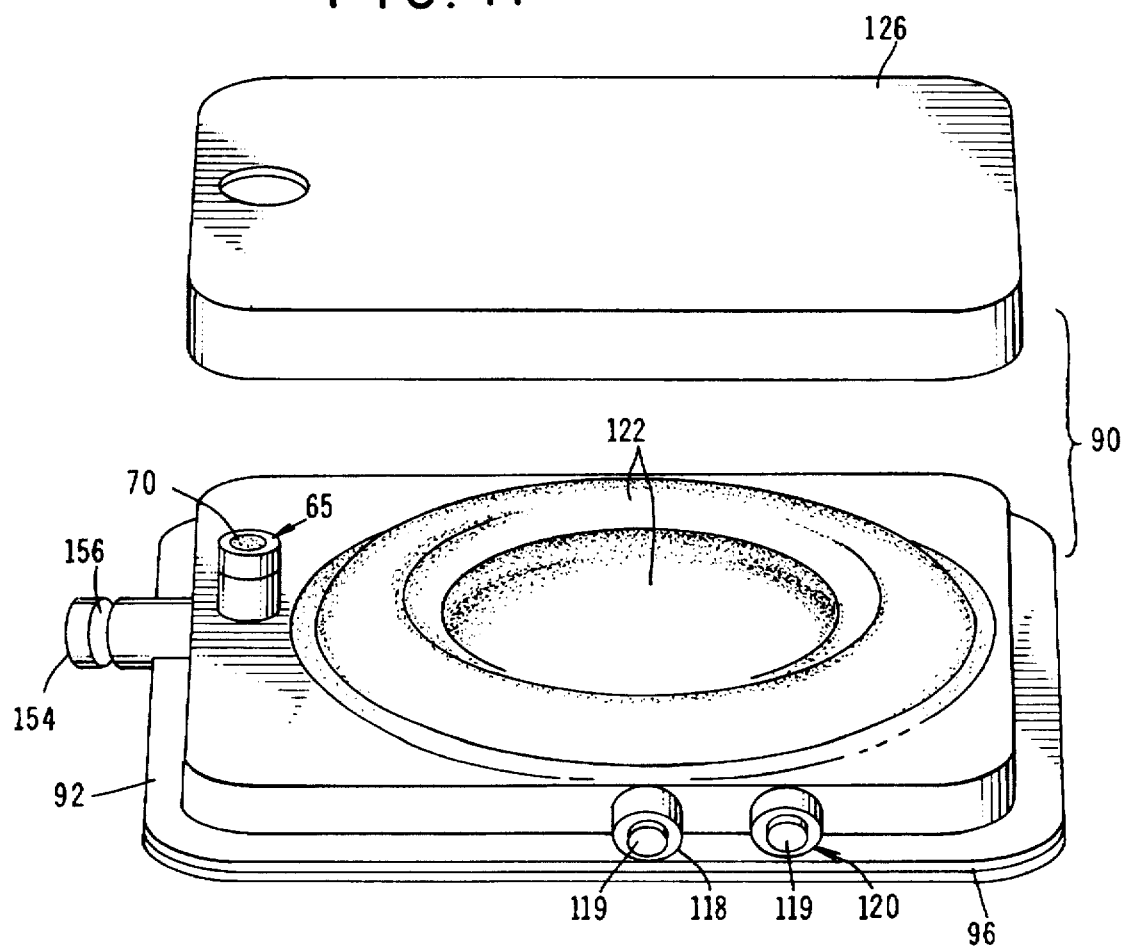
FIG. 11 is a generally perspective, exploded view of an alternate embodiment of the invention.

During the fluid dispensing step, the distendable membrane will provide a constant fluid expelling pressure on the fluid contained within the reservoir throughout the fluid delivery cycle, thereby providing precise delivery of liquid medicament over the prescribed delivery period. In the manner discussed in U.S. Pat. No. 5,279,558, distendable membrane 28 can be tailored to provide the desired fluid flow characteristics. (See for example Column 17 of the patent.) During the liquid delivery step, fluid will flow from reservoir 20, through outlet port 32, through the previously identified flow control means and then into outlet passageway 34 (FIG. 10). The flow control means, which further controls the fluid flow characteristics of the device, here comprises an assemblage 36 which is received in a cavity 61 formed in base 12 and which is preferably constructed from a plurality of stacked members 36a, 36b, and 36c. Member 36a is a porous member; member 36b is a rate control element; and member 36c is a porous supporting substrate. Member 36a is preferably constructed from a material comprising polysulfone sold by Gelman Sciences under the name and style of "SUPOR". Member 36c is preferably constructed from a porous polycarbonate material available from Corning Costar Corporation or from a material sold by DuPont under the name and style KAPTON which has been laser drilled or machined to provide appropriate flow orifices. Member 36c can be constructed from a porous polypropylene. After flowing through the flow control means, the liquid medicament will flow outwardly of the device via passageway 34 and the infusion means in the manner best seen in FIG. 8.

An important feature of the apparatus of the present invention comprises the previously mentioned bolus injection means which here comprises a bolus injection site mounted in cover 40 and base 12 and generally designated by the numeral 65. Referring particularly to FIGS. 1 and 5, this novel bolus injection means includes a tapered cavity 67 provided in base 12 within which a pierceable septum 70 is mounted. A peripheral groove, or guide channel, 72 is provided in cover 40 and surrounds septum 70. Septum 70 is accessible via an opening provided in cover 40 and channel 72 is specially designed to guidably receive a first skirt portion 74a of a novel adapter means or adapter assembly 74 which also comprises a part of the bolus injection means of the invention. Adapter assembly 74 includes a central body portion 74b which supports a double-ended hollow needle 76. For purposes presently to be described, needle 76 has a pierceable point 76a at one end and a pierceable point 76b at the other end. A second internally threaded skirt portion 74c extends from central body portion 74b and surrounds end 76a of needle 76.

Turning to FIG. 1, it is to be noted that second skirt portion 74c is specially designed to be threadably interconnected with the threaded barrel portion "B" of a syringe shown here as a dose indicating injection pen "IP" of the character disclosed in U.S. Pat. No. 5,226,896 issued to Harris. While any type of conventional syringe assembly having an injection needle can be used to provide the bolus dose via septum 70, the apparatus of the present form of the invention is specially well suited for use with the Harris injection pen. For this reason, the Harris U.S. Pat. No. 5,226,896 is hereby incorporated by reference as through fully set forth herein.

In accomplishing the bolus delivery using the Harris device, internally threaded second skirt 76c of the adapter assembly is first threadably connected to barrel "B" of the Harris device. During this step, end 76a of the needle will pierce the septum of a medicament vial disposed within the device IP. Next, the adapter assembly is mated with cover 40 by inserting first skirt 74a into groove 72 and then pressing inwardly on the pen to cause needle end 76b to pierce septum 70. This places the bore of the hollow needle in communication with the passageway 34 formed in base 12 and also in communication with bore 50 of fitting 48 of the infusion means. Operation of the injection pen "IP" in the manner described in U.S. Pat. No. 5,226,896 will then cause a bolus dose to enter the infusion means for delivery to the patient.

With this highly novel construction, the patient can receive from liquid reservoir 20 a selected basal dose of insulin of, by way of example, one-half milliliter over a 24 hour period. Should the patient determine that the blood sugar level is unduly high, a bolus injection of a predetermined volume can quickly and easily be accomplished through use of the bolus injection means of the invention thereby appropriately supplementing the basal dose being delivered from the fluid reservoir 20.

More particularly, by using either a conventional syringe or by using the injection pen IP, a bolus dose can be introduced into fluid passageway 34 via septum 70. Because of the resistance to upstream flow offered by the rate control means, the bolus dose will flow through passage 34 toward the central bore 50 of quick connect fitting 48 and thence into delivery line 54. Interconnected with line 54 is a soft cannula assembly 80 (FIG. 8), the operation of which is well understood by those skilled in the art. Once the soft cannula 80a has been introduced into the patient's subdermal tissue "ST" in the manner shown in FIG. 8, the cannula insertion assembly 82, which includes a trocar 82a can be removed, leaving the soft cannula 80a in position within the patient. Needle cannula interconnect 84a of the connector assembly 84 of the infusion set can then be inserted into assembly 80 and interconnect therewith using the conventional latch mechanism 85. Connector assembly 84 which also forms a part of the infusion means, when connected to assembly 80, places soft cannula 80a in fluid communication with reservoir 20. The infusion set of this form of the invention, which comprises line 54, connector assembly 84, and soft cannula assembly 80, is of a character well known in the art and is readily available from several commercial sources including Pharma-Plast International A/S of Lynge, Denmark.

Figure 10A:
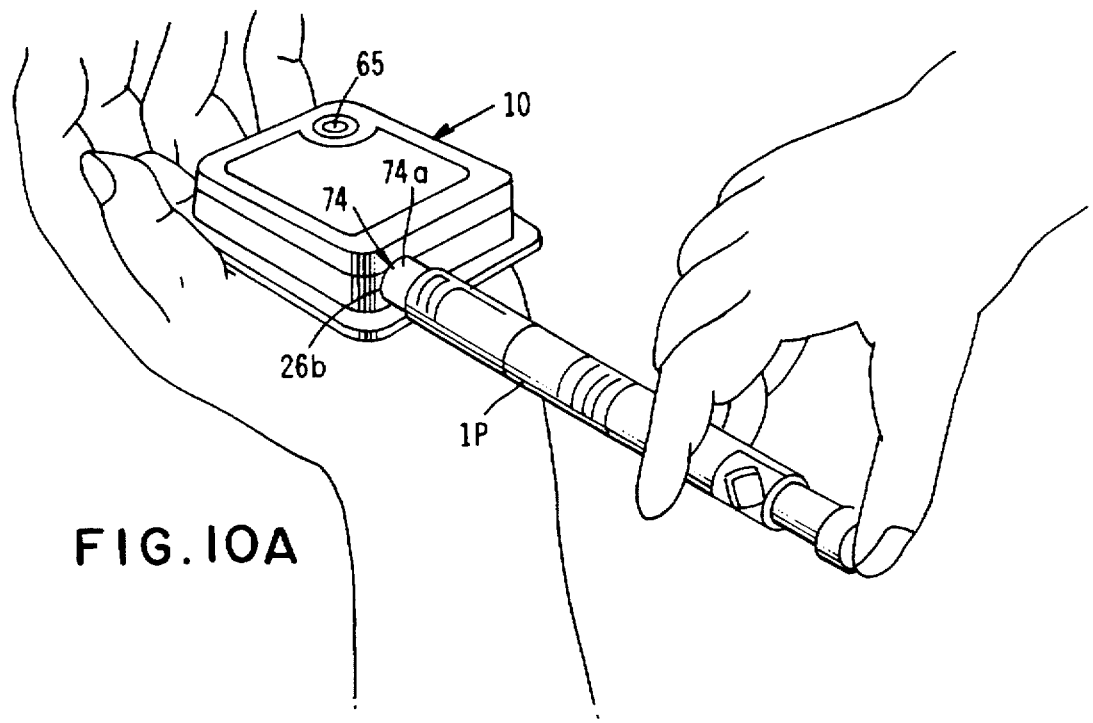
FIG. 10A is a generally perspective, illustrative view showing one manner of filling the fluid reservoir of the device.
Figure 10B:
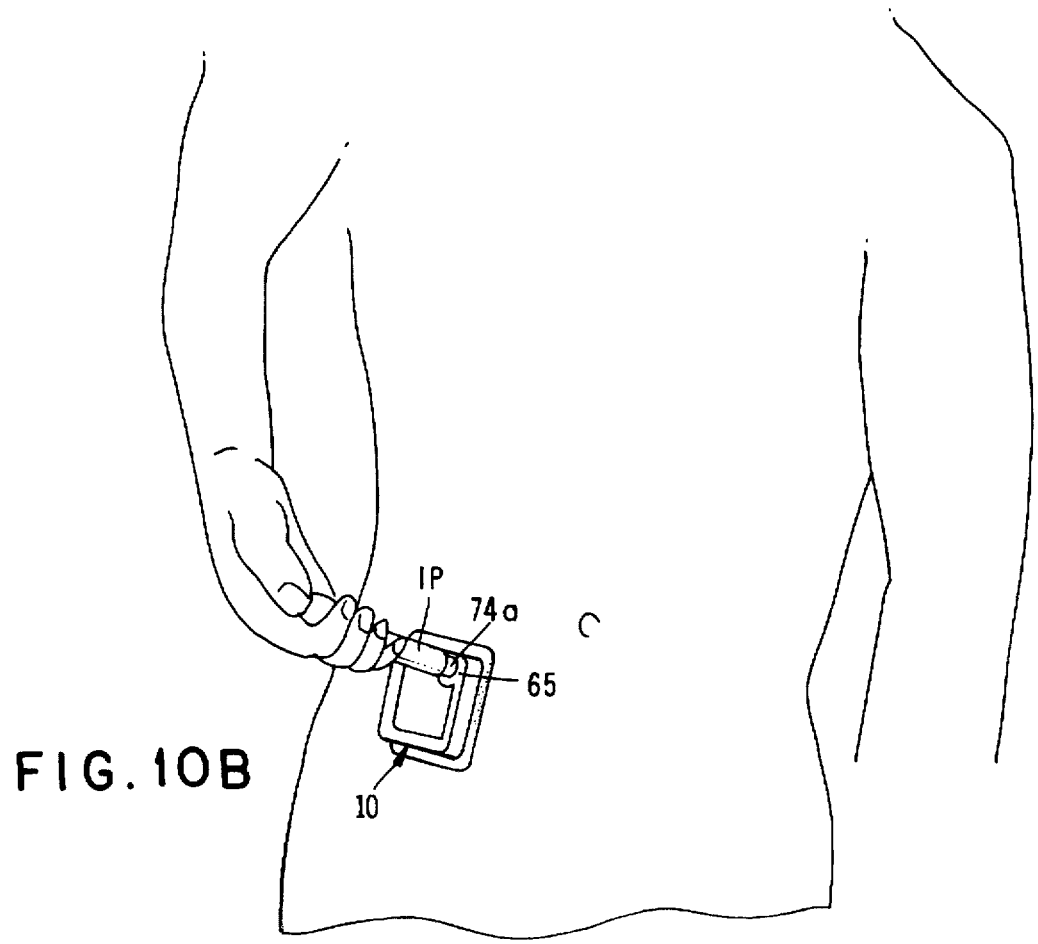
FIG. 10B is a generally perspective, illustrative view showing the device of the invention attached to the patient and showing the patient engage in injecting a bolus dose of liquid medication.

Turning to FIG. 10B, it is to be noted that the injection pen IP can effectively be used to provide the bolus dose delivery when the device of the invention is affixed to the patient's body as, for example, a location proximate the patient's waist. Due to the novel design of the skirt portion 74a of the adapter assembly 74, the injection pen can be easily mated with device 10 by simply inserting the skirt portion into the circular guide channel or groove 72.

As illustrated in FIG. 10A, the injection pen IP can also be conveniently used to fill the fluid reservoir of the device via filling septum 26a while being held in the user's hand. In this case, skirt portion 74a is guidably received within guide channel 26b formed as a part of septum assembly 26 (see also FIG. 4).

Referring next to FIGS. 11 through 17, still another form of the fluid delivery device of the invention is there shown and generally designated by the numeral 90. As best seen by referring to FIGS. 11 and 12, this latest embodiment of the invention is similar in some respects to that shown in FIGS. 1 through 10. Accordingly, like numbers are used to describe like components. However, this latest embodiment of the invention is unique in that it includes dual reservoirs which communicate with the infusion means of this latest embodiment of the invention.

Figure 12:
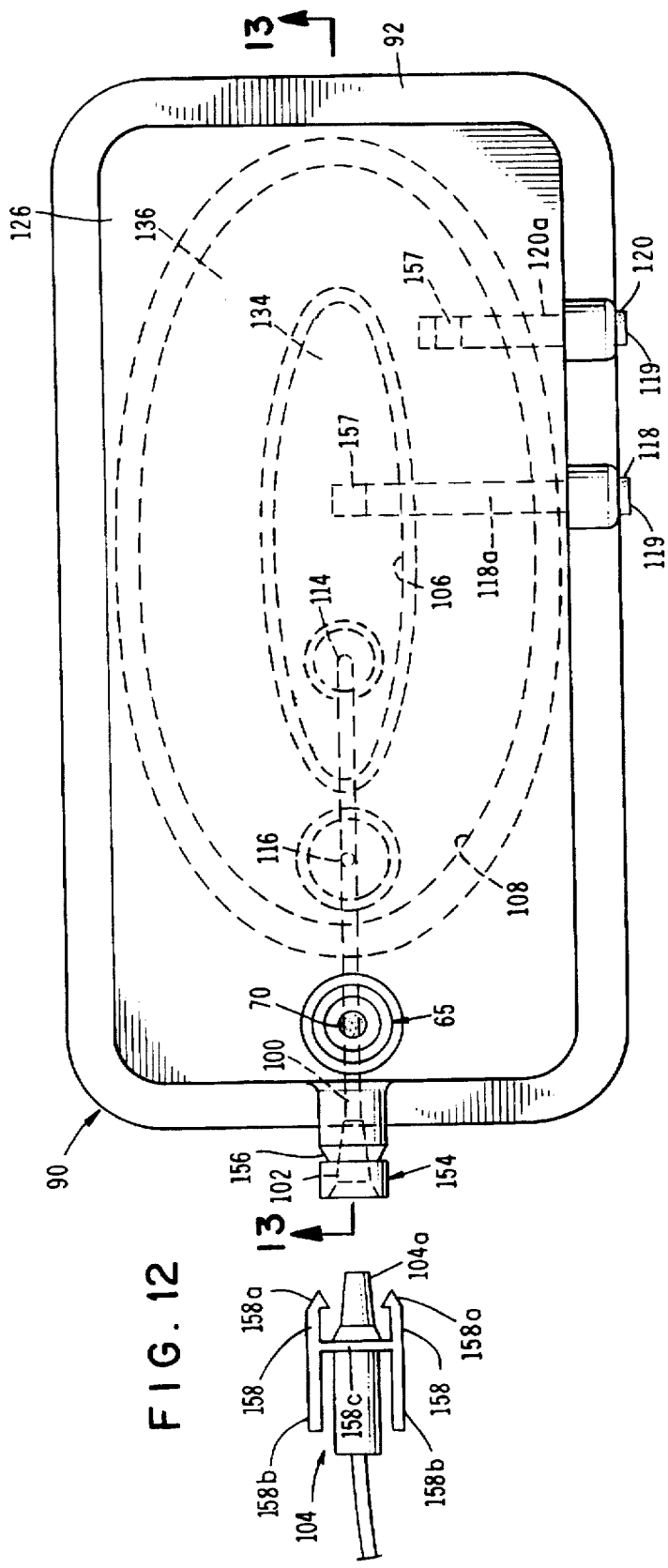
FIG. 12 is a top view of the embodiment shown in FIG. 11 partly broken away to show internal construction.
Figure 13:
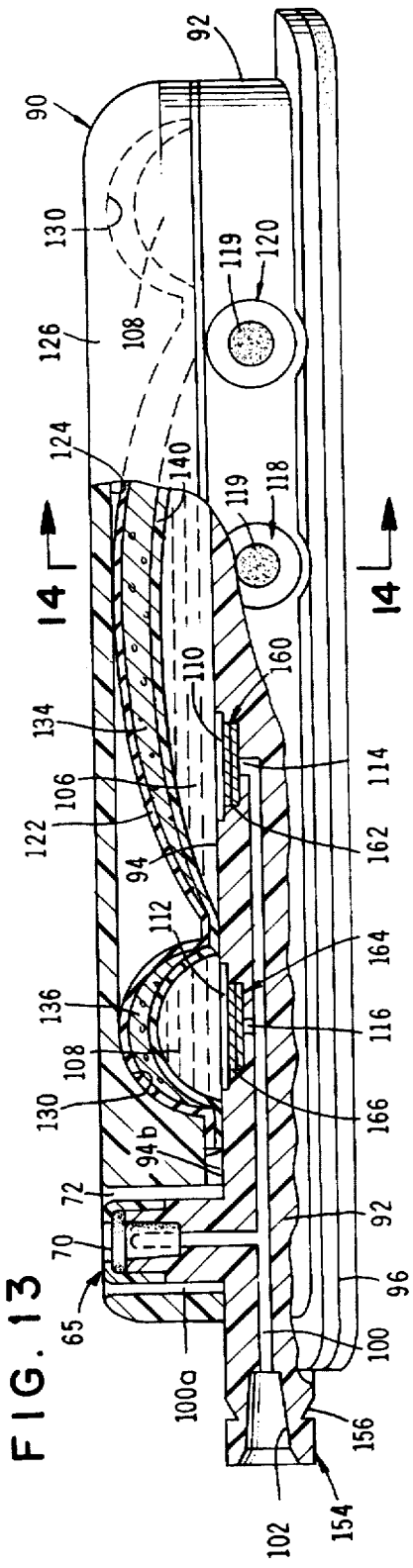
FIG. 13 is a side elevational, partly cross-sectional view taken along lines 13—13 of FIG. 12.
Figure 14:
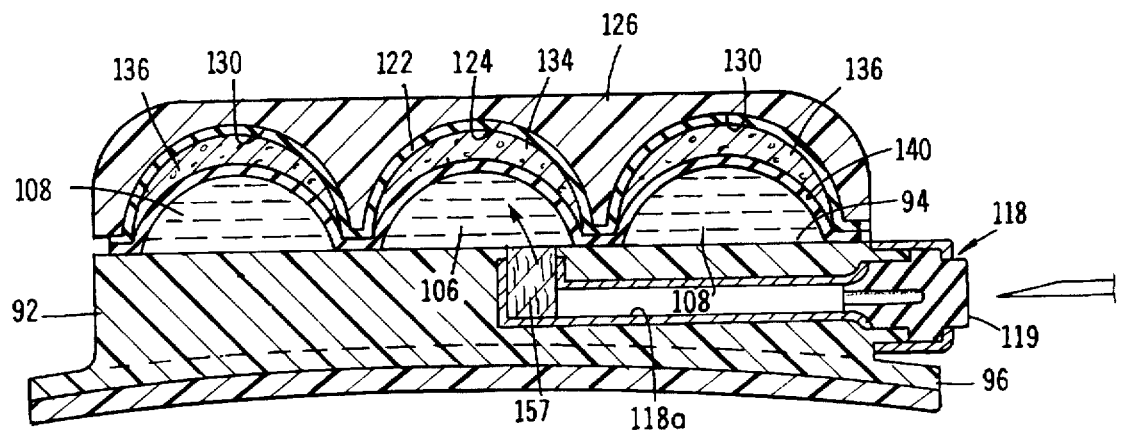
FIG. 14 is a cross-sectional view taken along lines 14—14 of FIG. 13.

As best seen in FIGS. 12 and 13, the embodiment of the invention there shown comprises a base 92 having an upper surface 94 including a central portion 94a and a peripheral portion 94b circumscribing central portion 94a. Base 92 is also provided with a lower surface 96. Formed within base 92 is a fluid passageway 100 (FIG. 12), which communicates with a tapered wall, cavity 102 provided in base 92, which cavity sealably receives portion 104a of a quick connect delivery fitting assembly 104 which is somewhat similar to fitting 48 as previously described.

As before, the apparatus shown in FIGS. 11 through 17 includes stored energy means for forming, in conjunction with the base 92, a pair of reservoirs 106 and 108 having outlets 110 and 112 respectively (FIG. 13). As best seen in FIG. 13, outlet 110 is in communication with a first inlet passageway 114 leading to passageway 100, while outlet 112 is in communication with a second inlet passageway 116 leading to passageway 100. Filling of central or inner reservoir 106 is accomplished via fill means here comprising a first septum assembly 118 while filling of outer or toroidal reservoir 108 is accomplished via a second fill means or second septum assembly 120. Both septum assemblies include a pierceable septum 119 (FIG. 14) which is pierceable by a needle of a conventional syringe.

As before, the stored energy means is provided in the form of at least one distendable membrane 122 which is superimposed over base 92. An ullage defining means is disposed within a central chamber portion 124 formed in a cover 126 for forming ullage within the chamber. Similarly an ullage defining means is disposed within a peripheral chamber portion 130 formed in cover 126 each of the central chambers for forming ullage within the toroidal chamber. The ullage means interact with membrane 122 which, after being distended, will tend to return to its less distended configuration. The ullage defining means of this latest embodiment of the invention comprises conformable masses 134 and 136 which uniquely conform to the continuously changing shape of the distendable membrane as the membrane tends to return to its less distended configuration. The first conformable mass 134 is disposed within chamber 124, while the second conformable mass 136 is disposed within chamber 130. The ullage defining means, or flowable masses 134 and 136 are preferably constructed from materials such as gels, foams, fluids and soft elastomers. More particularly, materials particularly well suited for constructing the conformable masses include oil, gaseous materials, various polymers and various viscous liquids. Additionally, those masses can be formed from sodium palmitate, sodium sterate and methyl cellulose. Where, as is here the case, the conformable ullage comprises a gel, a yieldable encapsulation barrier means or membrane 140 is used to encapsulate the conformable masses 134 and 136 between the distendable membrane and the barrier membrane. With this construction, the conformable ullages are located between the barrier membrane 140 and the distendable membrane 122. Barrier membrane 140 can be constructed from various materials including polyurethane, polypropylene, polyethylene and fluorosilicon.

Figure 15:
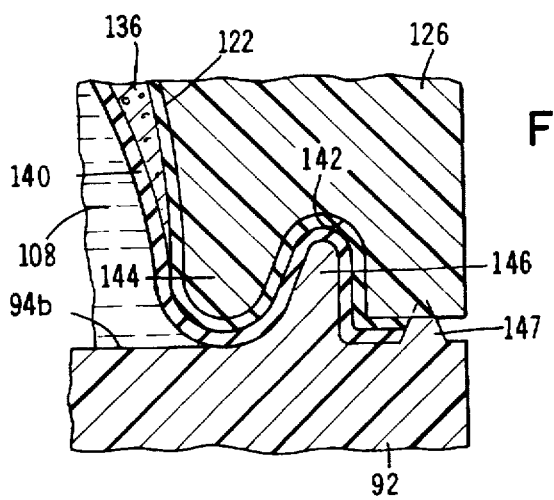
FIG. 15 is a greatly enlarged, fragmentary, cross-sectional view of a portion of the base and cover of the device illustrating the manner in which the distendable membrane and the barrier membrane of the device are sealably clamped between the base and cover.
Figure 16:
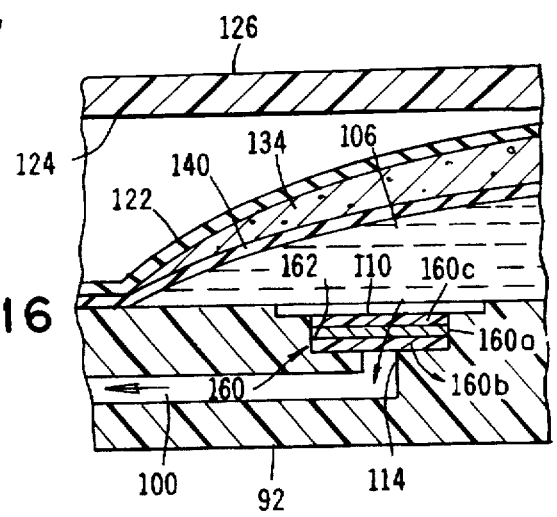
FIG. 16 is a fragmentary, cross-sectional view of the flow control assembly of the device which is positioned within the base.

As indicated in FIG. 15, the peripheral portion of the cover 126 is provided with a capture groove 142 and an adjacent tongue 144. Similarly, base 92 is provided with tongue 146 which mates with groove 142 as the cover moves into engagement with base 92. Base 92 is further provided with an upstanding membrane cutting means, or protuberance 147 which functions to cleanly cut the stored energy means and barrier membrane 140 upon cover 126 being brought into pressural engagement with base 92. With this construction, following cutting of the membrane the cover can be sonically welded to the base in a manner well understood by those skilled in the art.

In using the apparatus of this latest form of the invention, central reservoir can be filled via septum assembly 118 and passageway 118a using a conventional fluid containing syringe assembly having needle adapted to penetrate septum 119 of septum assembly 118. Similarly, toroidal reservoir 108 can be filled via septum assembly 120 and passageway 120a using a second syringe assembly containing a second fluid either the same as or different from the first fluid used to fill chamber 106. Fluids flowing into the reservoirs are filtered by filter means shown in FIG. 14 as filter elements 157. With the chambers filled, and the quick connect delivery fitting assembly 104 connected to base 92, the device is in condition for the liquid delivery step. As seen in FIG. 12, the quick connect delivery fitting assembly is of slightly different construction, as is the outlet port assembly of the device. More particularly, the outlet port housing 154, within which tapered portion 102 is formed, extends outwardly from the base and is provided with a circumferentially extending locking groove 156 which forms a part of the infusion set locking means of this form of the invention. Fitting assembly 104 also includes a pair of spaced-apart locking arms 158 which terminate at their inboard ends in hook-like extremities 158a which are receivable within groove 156. By pressing inwardly on the rearwardly extending portions 158b of arms 158, extremities 158a will pivot about a collar 158c carried by the fitting and will resiliently spread apart to permit their release from normal biased engagement with groove 156. As before, the base of the device is provided with a suitable adhesive to enable the device to be removably affixed to the patient's body such as to the arm or leg of the patient.

Once the device is interconnected with the patient, it will be appreciated that the fluids contained within first or central chamber 106 and within toroidal chamber 108 will be urged to flow through fluid passageway 100 as the stored energy means, or distendable membrane 122 tends to return to its less distended configuration. As before, the conformable ullages contained within the reservoirs will closely conform to the changing geometry of the stored energy means as the stored energy means moves toward base 92.

Figure 17:
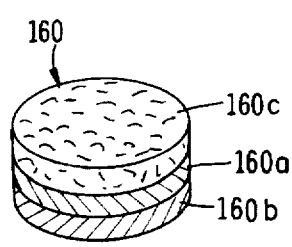
FIG. 17 is an enlarged, generally perspective view of the flow control assembly shown in FIG. 16.

The flow control means here comprises a pair of assemblies each being of the character shown in FIG. 17. Each assembly is receivable within a cavity provided in the base. More particularly, assemblage 160 is mounted within a cavity 162 provided in the central portion of the base while assembly 164 is mounted within a cavity 166 provided in the peripheral portion of the base. As shown in FIG. 17, each assemblage 160 and 164 is of a laminate construction comprising filtering means for filtering the fluid flowing outwardly of the reservoirs and rate control means for controlling the rate of fluid flow from the reservoirs into passageway 100. Referring to FIG. 17, it can be seen that the filter means comprises disk-like filter element 160a while the rate control element comprises a disk-like rate control element 160b. A porous disk-like support substrate 160c provides support to elements 160a and 160b. The assemblage comprising filter element 160a, rate control element 160b and porous substrate 160c is supported in base 92 in the manner shown in FIG. 16. Filter element 160a can be constructed from a wide variety of materials. However, a material comprising polysulfone sold by Gelman Sciences under the name and style of SUPOR has proven satisfactory. Rate control element 160b is preferably constructed from a polycarbonate material having extremely small flow apertures ablatively drilled by an excimer laser ablation process. Both the orifice size and unit distribution can be closely controlled by this process. However, a number of other methods can also be used to construct this element. Porous substrate 160c can similarly be constructed from various materials such as a porous polypropylene available from Gelman Sciences.

The latest embodiment of the invention also includes bolus injection means comprising a bolus injection site 65, which is identical in construction and operation to that previously described. As before, the bolus injection means includes a pierceable septum 70 which is accessible through the cover of the device and also includes a guide channel 72 which permits easy mating of the previously described adapter assembly 74. As best seen in FIG. 13, liquids introduced via septum 70 will flow into a passageway 100a which communicates with outlet passageway 100, thereby permitting delivery to the patient of bolus doses of medication via the infusion means of the device.

Figure 18:
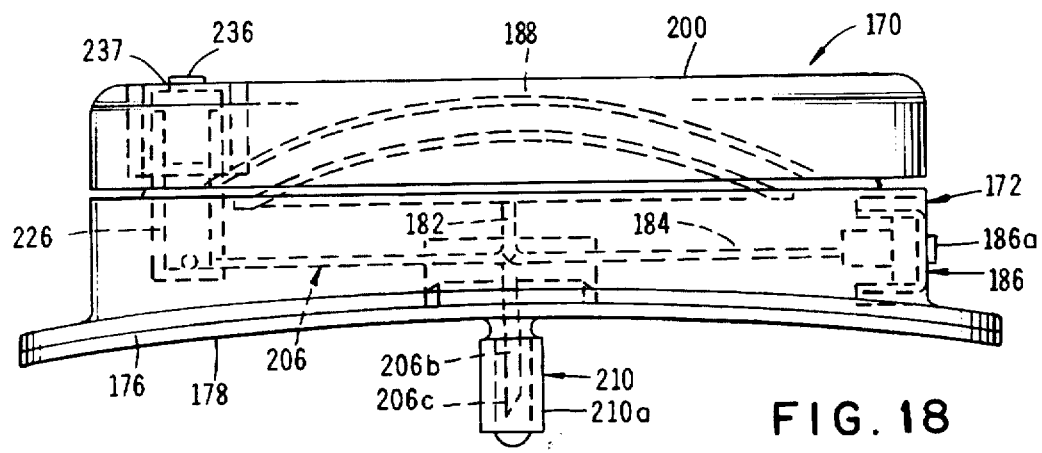
FIG. 18 is a front view of yet another form of the fluid delivery device of the invention partly broken away to shown internal construction.

Referring to FIGS. 18 through 24, yet another form of the fluid delivery device of the invention is there shown and generally designated by the numeral 170. This latest form of the invention is similar in many respects to that shown in FIGS. 1 through 10, but in this latest embodiment the infusion means is specially designed for subdermal infusion of selected medicaments. The device here comprises a base 172, having an upper surface 174 including a central portion 174a and a peripheral portion 174b circumscribing central portion 174a. As best seen in FIGS. 18 and 22, base 172 is also provided with a lower surface 176 to which a patient interconnection means or adhesive pad assembly 178 is connected. As before, pad assembly 178 functions to releasably interconnect the device to the patient so as to hold it securely in place during the delivery step.

Figure 19:
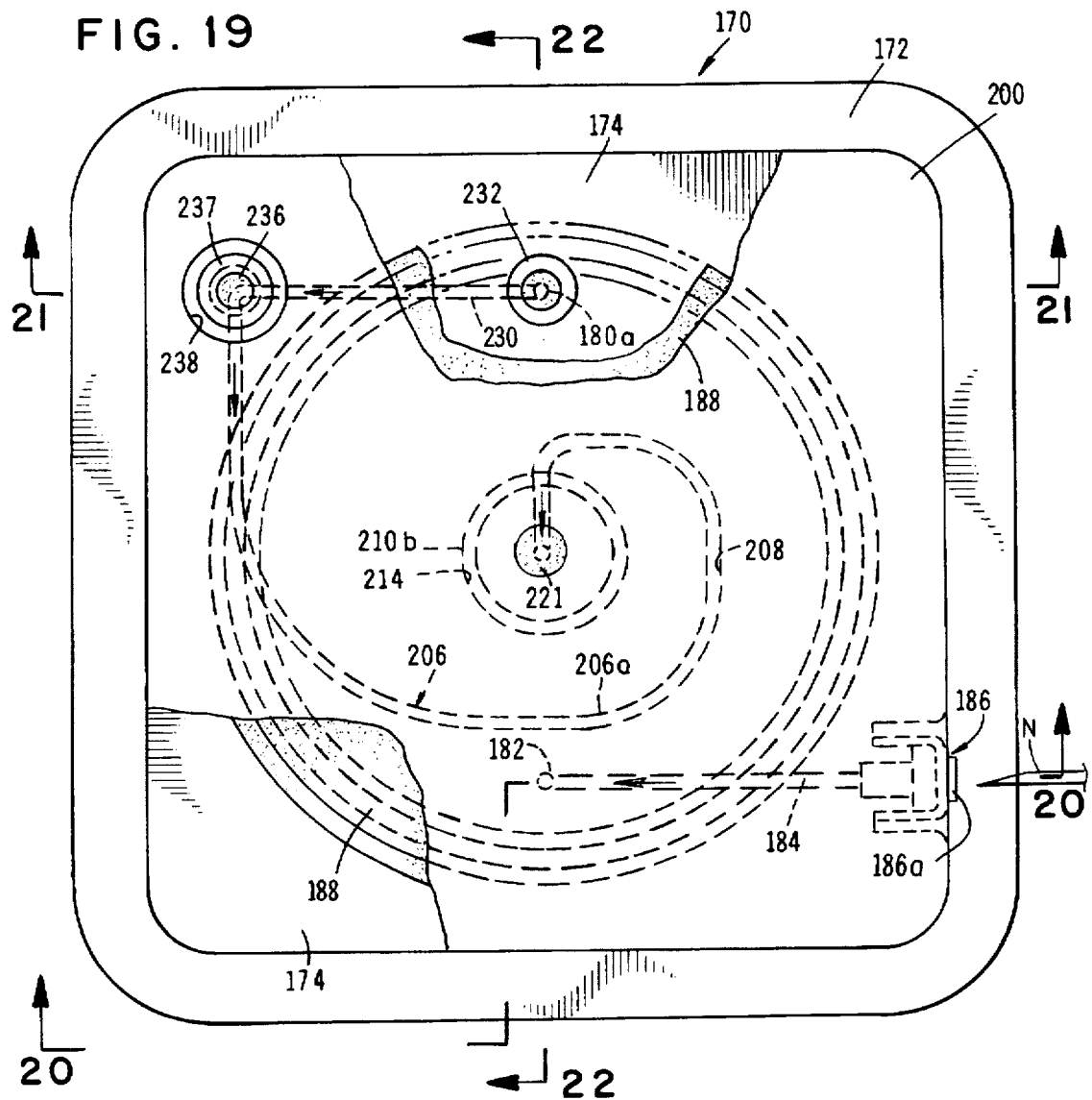
FIG. 19 is a top view of the embodiment shown in FIG. 18 partly broken away to show internal construction.

As was the case with the earlier described embodiments of the invention, a stored energy means cooperates with the upper surface 174 of base 172 to form a reservoir 180 having an inlet port 182 which is in communication with a flow passageway 184 which, in turn communicates with a filling means shown here as a septum assembly 186 (FIGS. 18, 19, and 20). The stored energy means is here provided in the form of at least one distendable membrane 188 which is superimposed over base 172. Membrane 188 is distendable as a result of pressure imparted on the membrane by fluids "F" introduced into reservoir 180 through inlet port 182 (FIG. 20). As membrane 188 is distended in the manner shown in FIG. 20, internal stresses will be established, which stresses tend to move the membrane toward a less distended configuration and in a direction toward base 172. Membrane 188 is substantially identical to membrane 28 (FIG. 3) and can be constructed from a single membrane or from multiple membranes to form a laminate construction.

Provided within the reservoir of the device, which is defined by the upper surface 174 of the base and a concave surface of a cover means for covering the distendable membrane, is ullage defining means for providing ullage within the reservoir and for engagement with membrane 188 as the membrane moves toward its less distended starting configuration. The ullage defining means provided in this latest embodiment of the invention comprises a conformable mass 190 which is engageable by the distendable membrane as the membrane returns to its less distended configuration. Conformable mass 190 is of a character similar to the conformable masses that make up the ullage defining means of the form of the invention shown in FIGS. 11 through 17. As before, when the distendable membrane returns toward its distended configuration, fluid contained within the reservoir 180 will flow uniformly outwardly of the reservoir through an outlet port 180a and into a fluid outlet passageway 230 via flow control means generally designated by the numeral 224 (FIG. 22A).

Superimposed over base 172 is the cover means, shown here as a rigid cover 200, which functions, through the use of novel sealing means, to sealably enclose membrane 188. The sealing means here comprises a circular groove 175 formed in peripheral surface 174b of base 172 and a circular rim like protuberance 200a formed on the lower surface of cover 200. Protuberance 200a is receivable within groove 175 and functions to sealably clamp distendable membrane 188 between the cover and the base in the manner shown in FIGS. 20 and 22. If desired, a medicament and use label 41 can be affixed to cover 200 in the manner previously described and as shown in FIG. 1. Once again, base 172 and cover 200 can be constructed from a variety of materials of the character described in U.S. Pat. No. 5,279,558.

Referring particularly to FIGS. 19 and 24, the infusion means of this latest form of the invention for subdermal infusion of medicaments into the patient is of a highly novel construction. More particularly, the infusion means here comprises a circuitous shaped hollow cannula 206 which is carried within a circuitous channel 208, formed in the intermediate body portion 172i of base 172. Cannula 206 includes a body portion 206a which is mounted within channel 208 and also includes an outlet end 206b, here provided in the form of a needle-like segment, which extends generally perpendicularly downward from the lower surface of base 172. The circuitous body portion 206a, of the cannula, when mounted within channel 208, provides an extremely strong and rigid structure that effectively prevents bending or breakage of the small diameter cannula. So that outlet end 206b can easily penetrate the patient's skin and tissue "ST" for subdermal penetration (see FIG. 22A), end 206b is provided with a sharp, pointed extremity 206c (FIGS. 22 and 22A).

To protect segments 206b and 206c of the cannula from damage, a protective cover assembly 210 surrounds these portions of the cannula. At time of use, the skirt portion 210a of the protective cover 210 can be readily separated from the base by breaking it away along a serration line 211 formed between the skirt portion 210a and a disk like base portion 210b. Skirt portion 210a is configured to receive a plug 210p which provides a sterile barrier and prevents premature fluid flow from end 206c of the cannula. Base portion 210b is provided with an upstanding circumferentially extending rim 210c which is receivable within a cylindrically shaped cavity 214 provided in base 172 (see FIG. 22). Disk-like base portion 210b is also receivable within an aperture 178a provided in pad assembly 178 (FIG. 23).

Filling of reservoir 180 is accomplished by introducing fluid into the reservoir under pressure via a septum assembly 186 which is mounted in base 172 (FIG. 18). Using an appropriate syringe assembly having a needle "N", fluid can be introduced into passageway 184 via a pierceable septum 186a which comprises a part of septum assembly 186. During this filling step, a barrier means or barrier membrane 217 is distended outwardly against the conformable mass 190 controllably moving it along with a distendable membrane 188 toward cover 200. As the ullage defining means moves toward cover 200, distendable membrane 188 will engage surface 219 formed in cover 200, and the ullage defining means will uniquely conform to surface 219 as well as to the varying shape of distendable membrane 188. As the distendable membrane moves toward surface 219 any gases contained within the reservoir will be vented to atmosphere via vent means, shown here as a vent plug 221. Barrier membrane 217 can be constructed from the various materials previously described.

When the fluid is dispensed from the device, the conformable ullage will permit the distendable membrane to provide a constant fluid expelling pressure on the fluid contained within the reservoir throughout the fluid delivery cycle, thereby avoiding undesirable delivery rate tail off at the end of the delivery period. This novel substantially linear performance permits the device to meet even the most stringent of delivery protocols. During the delivery step, fluid will flow from reservoir 180, through outlet port 192, through the flow control means, and then, in a manner presently to be described, into cannula 206. The flow control means of this latest form of the invention comprises an assemblage 224 which is received in a cavity 225 formed in the high novel fusion means of the present invention, the character of which will presently be described. Assemblage 224 comprises a first wafer 224a which functions as a filter means of the character previously described. Wafer 224b is preferably constructed from a hydrogel rate control medium which, upon imbibing fluid, swells into a cavity provided in the filter. Upon swelling into a known configuration, wafer 224b will function to provide a specific permeability thereby precisely controlling the rate of fluid flow from the reservoir 180. Wafer 224c functions as a support substrate for the assemblage.

Turning particularly to FIG. 24, the novel infusion means of the present invention is there illustrated. This infusion means includes the previously identified circuitous shaped cannula 206, the inlet end 206i of which is connected to a hollow housing 226 that is mounted in base 172 in the manner best seen in FIG. 21. Inlet end 206i of the cannula communicates with a chamber 226a formed in housing 226 as does the outlet end 230a of a hollow tube 230. The inlet end 230b of tube 230 is connected to a second hollow housing 232 which is mounted in base 172 and within which the previously identified cavity 225 is formed. With this construction, tube 230 places the outlet 180a of reservoir 180 in fluid communication with chamber 226a of housing 226 and also in fluid communication with cannula 206 via an inlet port 234 which is disposed within chamber 226a. Accordingly, fluid can flow from reservoir 180 into chamber 225 via the flow control means, then into tube 230 and finally into cannula 206 for subdermal delivery to the patient.

As before, an important feature of this latest form of the invention is the a bolus injection means which here forms a part of the infusion means of the invention and includes a bolus injection site which is accessible through cover 200. Referring particularly to FIGS. 21 and 24, it can be seen that this novel bolus injection means is similar to that previously described but includes the earlier identified hollow housing 226 within which a pierceable septum 236 is mounted in the manner shown in FIG. 21. Septum 236 is held in place within cover 200 by a retainer cap 237. A peripheral groove 238 surrounds retainer cap 237 and is specifically designed to receive the first skirt portion 74a of the previously described adapter means or adapter assembly 74. Adapter assembly 74 is of identical construction and operation to that described in connection with the embodiment of the invention shown in FIGS. 1 through 10 and serves to deliver a bolus dose of medicinal fluid into chamber 226a of hollow housing 226 and thence into cannula 206 via inlet 234. As before adapter assembly 74 is specially designed to be threadably interconnected with the dose indicating injection pen "IP" of the character disclosed in U.S. Pat. No. 5,226, 896 issued to Harris.

With the highly novel construction of the device as described in the preceding paragraphs, the patient can continually receive a selected basal dose of liquid medication, such as insulin from reservoir 180. However, should the patient at any time determine that his or her blood sugar level is unduly high, a bolus injection of a predetermined volume can quickly and easily be administered through use of the novel bolus injection means of the invention and in this way appropriately supplement the basal dose being delivered from reservoir 180.

Figure 25:
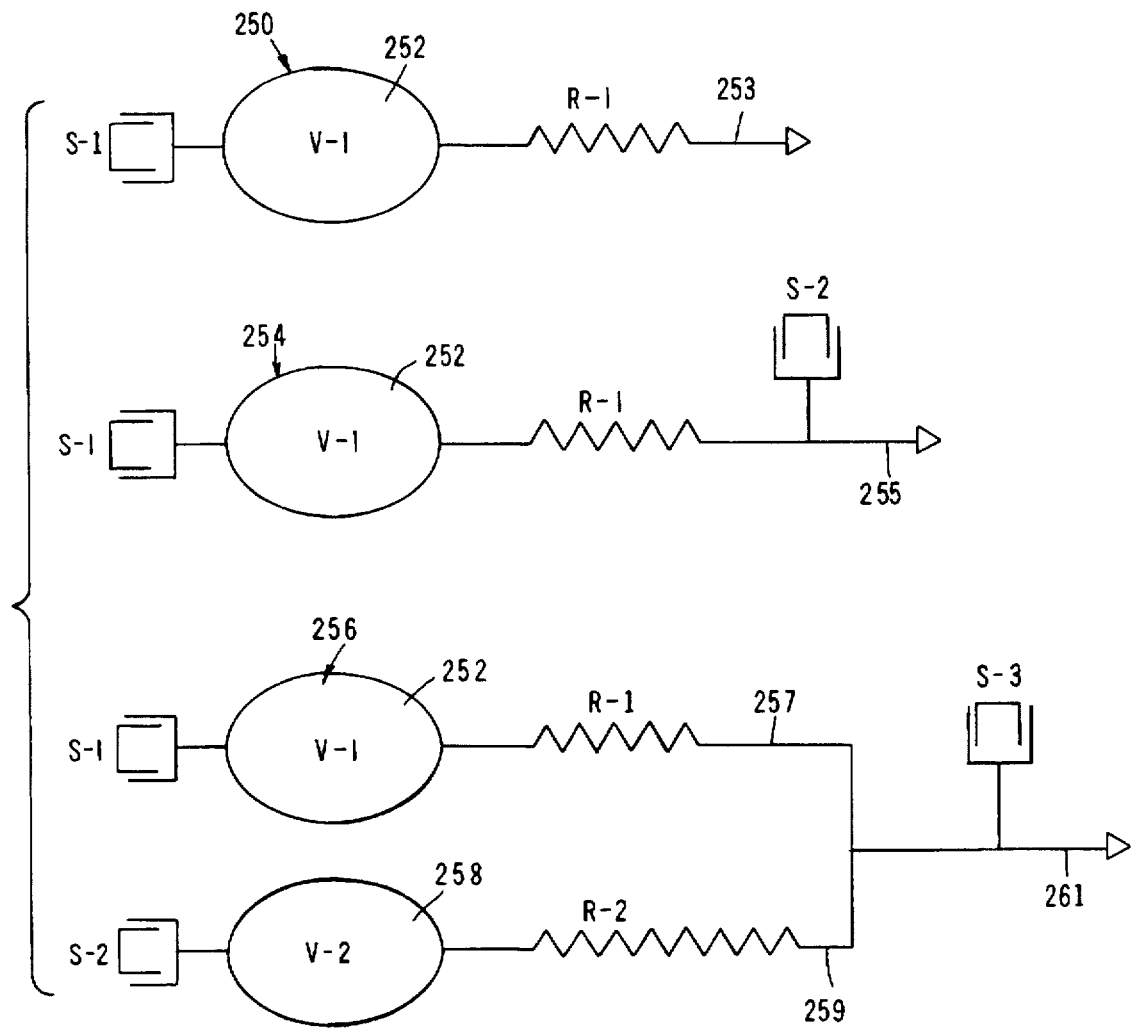
FIG. 25 is a generally schematic view illustrating the various modes of operation of the apparatus of the invention.

Turning finally to FIG. 25, several fluid delivery regimens are there illustrated. For example, at the upper portion of FIG. 25, a very simple regimen is illustrated. Here a fluid delivery device 250, having a fluid reservoir 252 with a volume V-1 is used to accomplish delivery of a liquid medicament such as insulin. The medicament is delivered to the patient through an appropriate infusion means which includes a delivery line 253 and a flow rate control means designated as R-1. Reservoir 252 can be filled using a filling means here shown as a septum assembly S-1. Using this basic arrangement, medicinal liquids can be delivered to the patient at a fixed rate over time with the rate of delivery being governed by the character of the flow rate control means R-1.

Referring next to the arrangement illustrated in the central portion of FIG. 25, a fluid delivery device 254 having a fluid reservoir 252 with a volume V-1 is there shown. As was the case with the previously described arrangement, fluid can be delivered to the patient at a basal rate via a delivery line 255 and a flow rate control means designated as R-1. Reservoir 252 can, once again, be filled by a fill means shown here is a septum assembly S-1. However, forming an important part of this second delivery system is a bolus dose delivery means generally designated as S-2. This bolus dose delivery means, which can be of the character illustrated and described in connection with the embodiment of the invention shown in FIGS. 1 through 10, uniquely enables the patient to administer a pre-determined bolus dose of liquid insulin as may be required. Device 254 exemplifies the types of single reservoir devices of the invention illustrated in FIGS. 1 through 10 and in FIGS. 18 through 24 of the drawings.

Turning to the last arrangement schematically illustrated in FIG. 25, a delivery device 256 is there provided. Unlike delivery devices 250 and 254, device 256 includes dual fluid reservoirs 252 and 258. As before, reservoir 252 has a volume V-1, while second reservoir 258 has a volume V-2. Reservoir 252 can be filled by septum assembly S-1 while reservoir 258 can be filled using a septum assembly S-2. Reservoir 252 communicates with the patient via a delivery line 257 and a first flow rate control means R-1, while reservoir 258 communicates with the patient via a delivery line 259 and a second flow rate control means designated as R-2. For reasons presently to be described, this arrangement is ideally for delivering liquid medicaments such as insulin. For example, during the day when a larger basal rate is required, insulin can be delivered to the patient via delivery line 261 with insulin flowing simultaneously from both reservoirs 252 and 258. The amount of fluid being delivered from each of the reservoirs is, of course, determined by the character of the flow rate control device which is interconnected with that reservoir. By making the resistance offered to fluid flow from reservoir 258 greater than the resistance to fluid flow from reservoir 252, it is apparent that reservoir 252 will empty faster than will reservoir 258. Accordingly, by correctly selecting the flow rate control means R-1 and R-2, reservoir 252 will be empty at the end of the day. However, because of the greater resistance offered by flow rate control means R-2, during the night insulin will continue to flow to the patient from reservoir 258 but at a lesser rate than the daytime basal delivery rate. Once again, by properly selecting the flow rate control means R-2, insulin can be delivered to the patient at a prescribed basal delivery rate from reservoir 258 throughout the entire nighttime hours. Thus a single dual reservoir fluid delivery device can be used to provide a precise basal delivery of insulin to the patient over an entire 24-hour period.

An important additional feature of this last arrangement, is the provision of a bolus dose delivery means designated as S-3. This important bolus delivery means permits the patient to introduce into delivery line 261 via S-3 a bolus dose of insulin at any time the patient discovers that his or her blood sugar level is too high. As is apparent, this latest arrangement as shown in FIG. 25, is exemplified by the dual reservoir embodiment of the invention which is illustrated in FIGS. 11 through 17 of the drawings.

In summary, it is clear from a study of FIG. 25 that each of the fluid delivery regimens illustrated in FIG. 25 and described in the preceding paragraphs can be accomplished using a selected one of the various embodiments of the invention disclosed in FIGS. 1 through 24 of the drawings.

Figure 31:
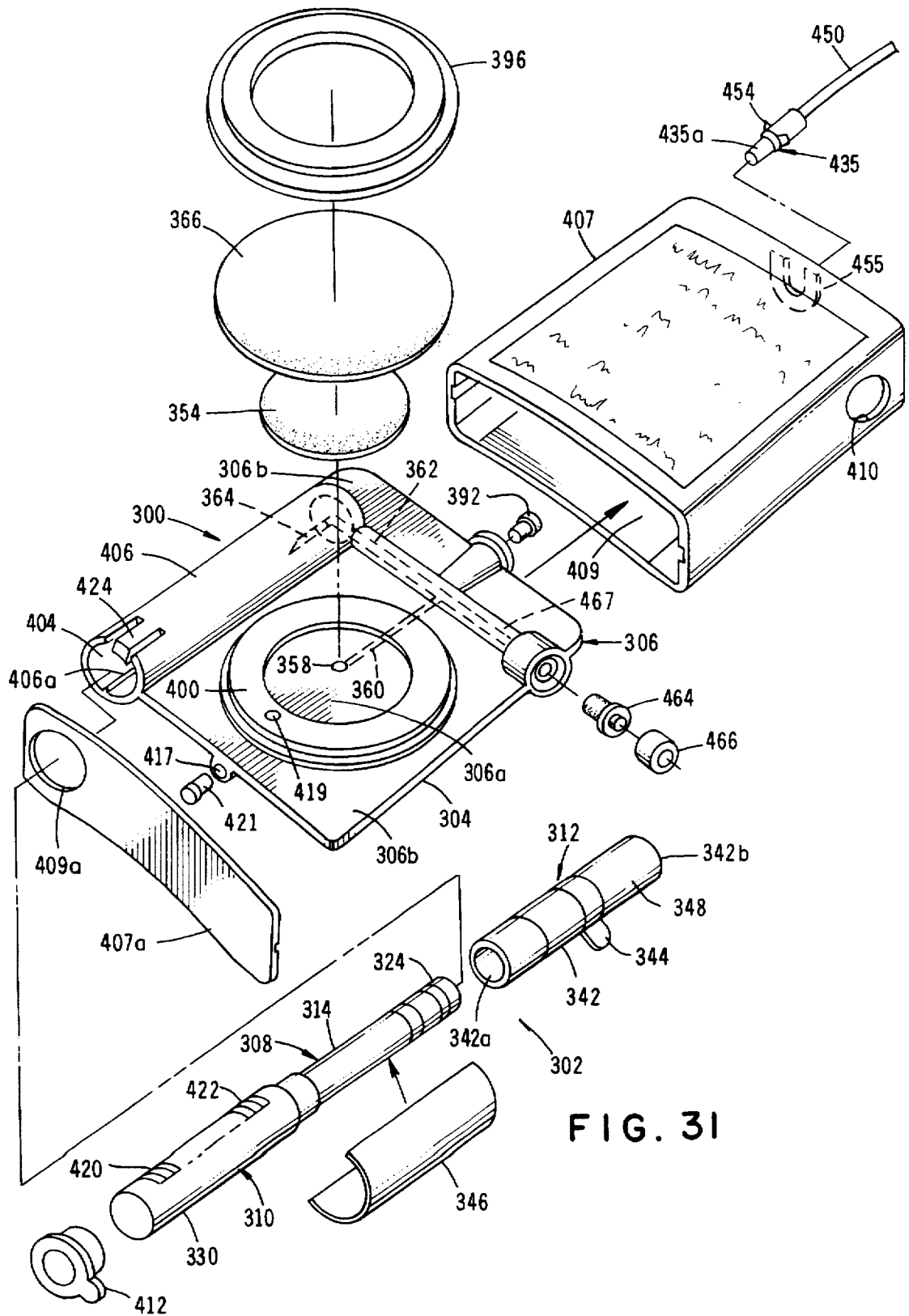
FIG. 31 is a generally perspective, exploded view of the apparatus of this latest form of the invention showing both the dispensing assembly and the fill assembly in an exploded configuration.

Referring next to FIGS. 26 through 41, yet another form of the apparatus of the present invention is there illustrated. The apparatus here comprises two main assemblies, namely a fluid delivery assembly 300 (FIGS. 26 and 31) and a fill assembly 302 (FIG. 27 through 30) which can be operably mated with the fluid delivery assembly in a manner presently to be described. Fluid delivery assembly 300, the details of construction of which will presently be described, is similar in some respects to the fluid delivery devices previously described herein and includes a base 304 having an upper surface 306 including a central portion 306a and a peripheral portion 306b (FIG. 31).

As best seen by referring to FIGS. 27 through 30, the fill assembly portion 302 of the apparatus comprises a container subassembly 308, an adapter subassembly 310, and a cover subassembly 312, the character of which will presently be described. Container subassembly 308 includes a body portion 314, having a fluid chamber 316 for containing an injectable fluid "F" which is provided with first and second open ends 318 and 320 (FIGS. 28 and 30). First open end 320 is sealably closed by closure means here provided in the form of a pierceable septum assembly 322. Septum assembly 322 is held securely in position by clamping ring 324.

As best seen in FIGS. 28 and 30, a plunger 326 is telescopically movable within chamber 316 of container subassembly 308 from a first location shown in FIG. 28 where it is proximate open end 318 to a second position shown in FIG. 30 where it is proximate open end 320. The vial portion of the container subassembly can be constructed of various materials including glass and plastic.

Referring particularly to FIGS. 27 and 28, it can be seen that the adapter subassembly 310 comprises a hollow housing 330 having a first open end 332 and a second closed end 334 (FIG. 30). Container subassembly 308 is telescopically receivable within open end 332 of housing 330 in the manner shown in FIG. 28 so that the housing can be moved from the first extended position shown in FIG. 28 to the vial encapsulation position shown in FIG. 30. Forming an important part of the adapter subassembly is pusher means shown here as an elongated pusher rod 336 which functions to move plunger 326 within fluid chamber 316 from the first position shown in FIG. 28 to the second position shown in FIG. 30. In the form of the invention shown in the drawings, pusher rod 336 has a first end 336a interconnected with a closure wall 334 of housing 330 and an opposite end 336b which engages plunger 326 and causes telescopic movement of the plunger within chamber 316 of container subassembly 308 as housing 330 is moved from the extended position into the vial encapsulating position shown in FIG. 30.

As best seen by referring to FIGS. 27 and 29, the interior wall 330a of housing 330 is provided with circumferentially spaced-apart protuberances 340 which engage and center container subassembly 308 within housing 330. Due to the small surface area presented by protuberances 340, there is little frictional resistance to the sliding movement of container subassembly 308 relative to housing 330 as the housing is moved from the extended position shown in FIG. 28 into the vial encapsulating position shown in FIG. 30.

Referring particularly to FIG. 27, it is to be noted that cover subassembly 312 of the fill assembly of the present form of the invention includes a spiral wound, frangible portion 342 having a first open end 342a for telescopically receiving body portion 314 of container subassembly 308 (FIG. 28) and a second closed end 342b. Portion 342 initially circumscribes a major portion of container subassembly 308 in the manner best seen in FIG. 28. An integral pull tab 344 is provided to permit the spiral wound, frangible portion to be pulled from container subassembly 308 so as to expose a substantial portion of body 314. As best seen in FIGS. 27 and 28, a medicament label 346 circumscribes spiral wound portion 342 and serves to prevent accidental unwinding of the spiral portion from the container subassembly 308. However, upon pulling tab 344, the spiral portion will unwind and, in so doing, will tear medicament label 346 so that the spiral portion 342 of the covering as well as the cylindrical portion 348 which, also comprises a part of the cover assembly, can be slipped from the container subassembly 308 so as to expose to view septum assembly 322 (FIG. 30).

As shown in FIGS. 27 and 28, end 342b of cylindrical portion 348 of subassembly 312 is provided with venting apertures 350 which are covered by a porous vent patch 352 which can be constructed from any suitable porous material that will permit air entrapped within the interior of cover subassembly 312 to be expelled to atmosphere as the subassembly is placed over container subassembly 308.

Turning particularly to FIGS. 26 and 31 through 38, the fluid delivery assembly 300 of the apparatus of the invention can be seen to include the previously identified base 304 which defines upper surface 306.

Figure 35:
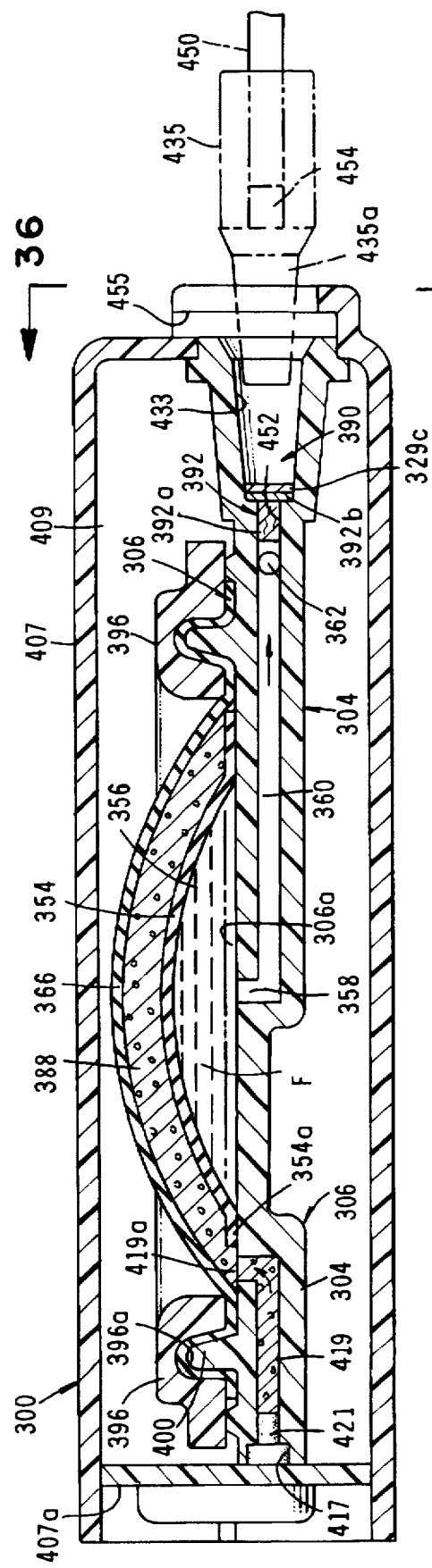
FIG. 35 is an enlarged, cross-sectional view taken along lines 35—35 of FIG. 32.

As was the case with the earlier described embodiments of the invention, a flexible barrier means, shown here as a barrier membrane 354, cooperates with the upper surface 306 of the base to form a reservoir 356 having an inlet/outlet port 358 which is in communication with flow passageways 360 and 362 the latter of which, in turn communicates with a cannula 364, the purpose of which will presently be described. (See FIGS. 31 and 35). A stored energy means is here provided in the form of at least one distendable membrane 366 which is superimposed over barrier membrane 354 and base 304. Disposed between barrier membrane 354 and distendable membrane 366 is an ullage defining means, shown here as a conformable mass 388 (FIG. 35). Conformable mass 388 is of a character similar to the conformable masses that make up the ullage defining means of the form of the invention shown in FIGS. 11 through 17 and can comprise a gel or other deformable material. Membrane 354 is distendable as a result of pressure imparted on the membrane by fluids "F" introduced into reservoir 356 through port 358. As membrane 354 is distended in the manner shown in FIG. 35, it will act on the conformable ullage, which will, in turn, act upon distendable membrane 366 causing internal stresses to be established, which stresses tend to move the membrane toward a less distended configuration and in a direction toward surface 306a of base 304. As before, membrane 354 can be constructed from a single membrane or from multiple membranes to form a laminate. When the distended membrane returns toward its less distended configuration, fluid contained within the reservoir 356 will flow uniformly outwardly of the reservoir through passageway 360 and then into a fluid outlet chamber 390 (FIG. 35) via flow control means generally designated by the numeral 392.

Superimposed over the central portion 306a of the base is sealing means, shown here as a sealing ring 396, which functions to sealably interconnect membrane 366 with base 304. Ring 396 includes a circular groove 396a within which is received a circular rim like protuberance 400 formed on the upper surface of base 304 (FIG. 35). Protuberance 400 is closely received within groove 396a and functions to sealably clamp distendable membrane 366 between the clamping rings and the base in the manner shown in FIGS. 35 and 38. As shown in these figures, the periphery 354a of barrier membrane 354 is sealably affixed to the base by any suitable means, such as adhesive or thermal bonding. Once again, base 304 and clamping ring 396 can be constructed from a variety of materials of the character described in U.S. Pat. No. 5,279,558.

Figure 32:
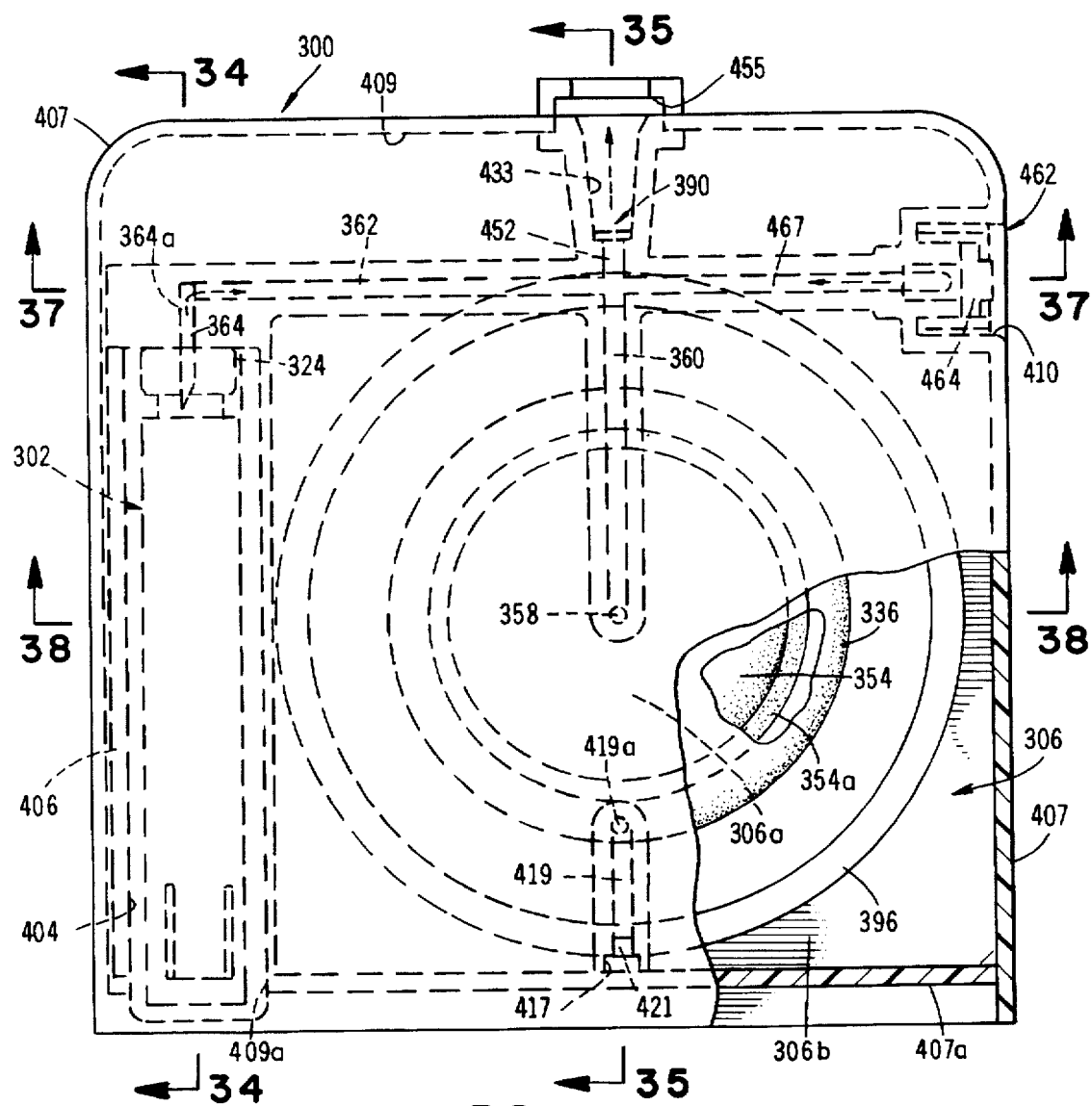
FIG. 32 is a top plan view of the assembled apparatus of the invention shown in FIG. 26 partly broken away to show internal construction.
Figure 33:
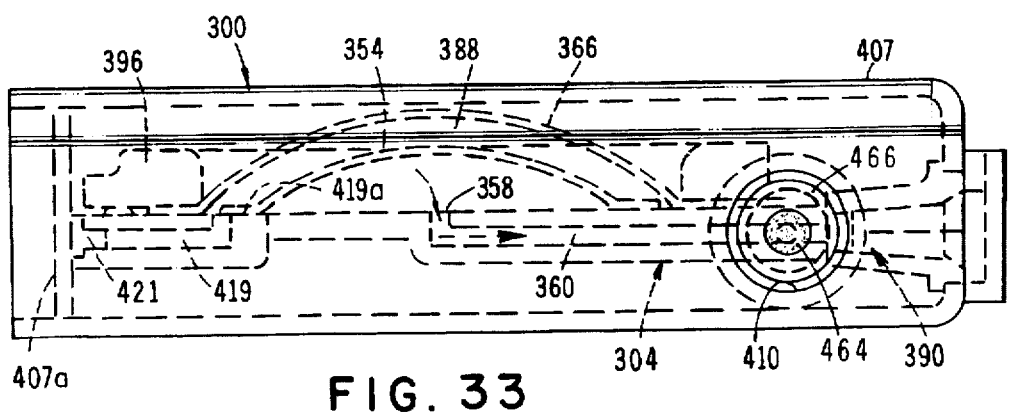
FIG. 33 is a right-side view of the apparatus shown in FIG. 32.
Figure 34:
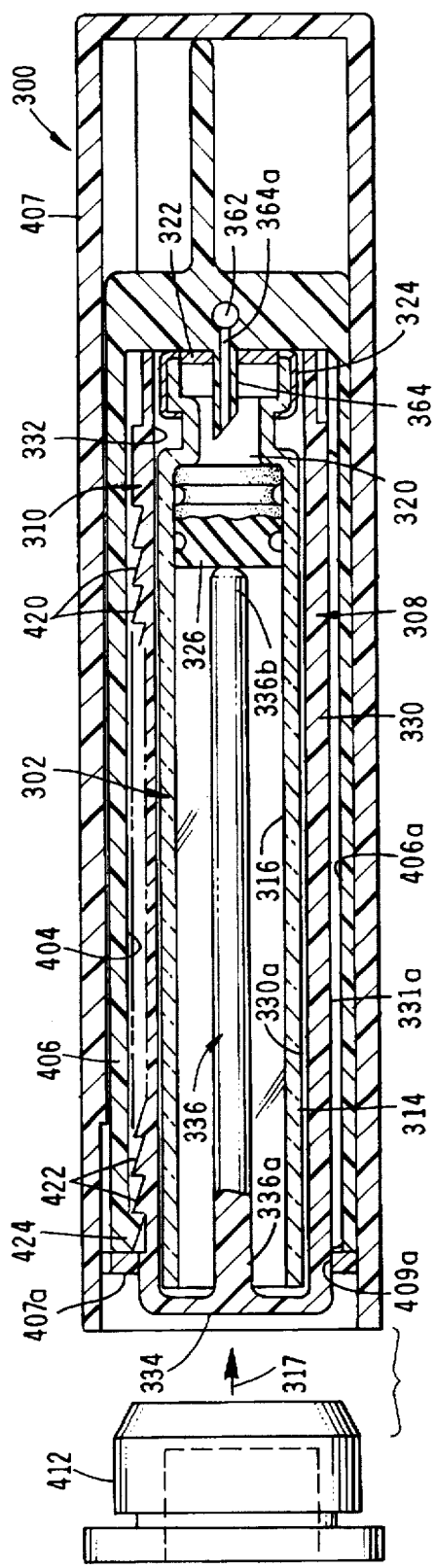
FIG. 34 is an enlarged, cross-sectional view taken along lines 34—34 of FIG. 32.

A unique feature of the base assembly of this latest form of the invention comprises, along one side of base 304, an elongated receiving chamber 404 which is adapted to receive a portion of the fill assembly of the invention. Receiving chamber 404 is formed within a generally cylindrically shaped housing 406 which is integrally formed with one of marginal portions 306b of the base. As best seen in FIGS. 31, 32, and 34, the previously identified piercing cannula 364 extends into the inboard portion of receiving chamber 404 and functions to provide a fluid flow path between the fill assembly and the fluid reservoir 356.

Turning particularly to FIGS. 31 and 35, the fluid delivery assembly 300 further includes a housing 407 having an internal chamber 409 within which the base assembly, including chamber 404, is received. An apertured end wall 407a substantially encapsulates the base assembly within chamber 409. End wall 407a includes an aperture 409a which is indexible with receiving chamber 404 when the base assembly is positioned within housing 407 in the manner shown in FIG. 32. Housing 407 is also provided with an aperture 410 which aligns with an important feature of the invention, namely a bolus injection means, the character of which will presently be described.

In using the apparatus of this latest form of the invention, with the fill assembly in the filled configuration shown in FIG. 28, the cover subassembly is first removed from the container subassembly by pulling on pull-tab 344. This will cause the spiral portion 342 of the cover subassembly to tear away from the container subassembly so that it can be separated from the forwardly disposed portion 348. Once the spiral wound portion 342 is removed, cylindrical portion 348 can also be removed and discarded. Removal of the cover subassembly to expose the forward portion of the container subassembly and septum 322 readies the adapter subassembly for interconnection with the fluid delivery assembly.

Prior to mating the adapter subassembly with the fluid delivery assembly, a closure plug 412 which forms a part of the cover subassembly must be removed in the manner illustrated in FIG. 26. This done, the container subassembly 308 can be telescopically inserted into receiving chamber 404 and pushed forwardly in the direction indicated by the arrow 314 in FIG. 34. A force exerted in the direction of the arrow will cause the adapter subassembly to move to the right as viewed in FIG. 34 and will cause the piercing cannula 364 to pierce septum 322. Once a fluid flow path between fluid chamber 316 of the container subassembly 308 and the fluid reservoir 356 of the fluid delivery assembly is thus created, a continued movement of the adapter subassembly will cause pusher rod 336 to move plunger 326 forwardly of chamber 316 to a position shown in FIG. 34. As plunger 326 is moved inwardly of chamber 316, the fluid "F" contained within the chamber will flow through open end 320, into passageway 364a of the piercing cannula, into passageway 362 of base 304 and then into fluid reservoir 356 via passageway 360. As the fluid under pressure flows into reservoir 356, barrier member 354 will be distended outwardly in the manner shown in FIG. 35 and will deform the conformable ullage 388 and at the same time distend the distendable membrane 366 until it reaches the position shown in FIG. 35. Gases contained in the volume between the cover and the distendable membrane will be vented to atmosphere via aperture 409a in end wall 407a. Ring 396, which is in clamping engagement with base 304, functions to capture and seal the distendable membrane relative to the base. In a similar manner, the periphery of the barrier member 354 is sealably affixed to the base as by adhesive or thermal bonding, so as to prevent leakage of fluid around the perimeter of the member.

Referring particularly to FIG. 35, it is to be noted that inlet means shown here as an inlet 417 formed in base 304 is provided to enable the introduction of gel which forms the conformable ullage 388 of this embodiment of the invention. Inlet 417 communicates with a fluid passageway 419 which, in turn, communicates with the volume defined between the under surface of membrane 366 and the upper surface of barrier member 354 via an inlet port 419a. Inlet 417 is sealably closed by a bonded plug 421.

Figure 38:
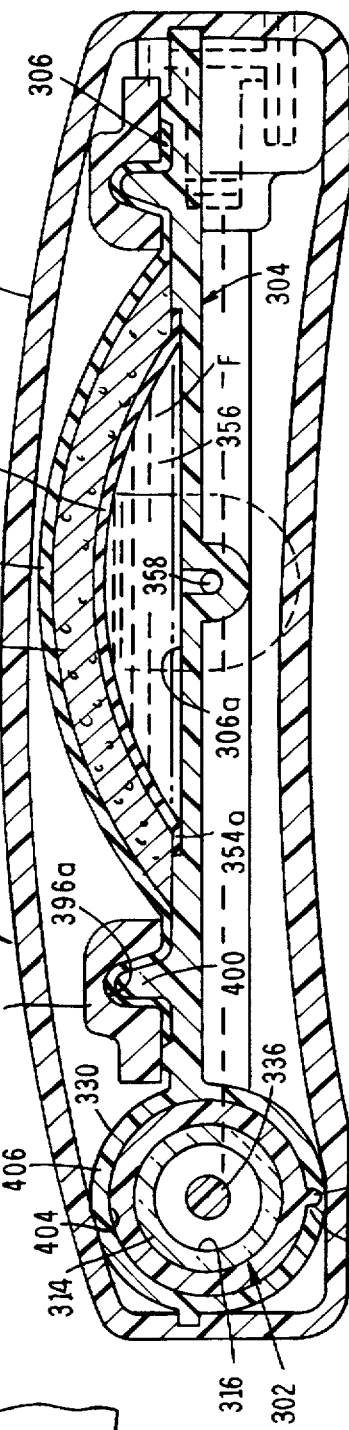
FIG. 38 is an enlarged, cross-sectional view taken along lines 38—38 of FIG. 32.

With the construction described in the preceding paragraphs and as shown in FIGS. 35 and 38, the conformable mass 388, which comprises the ullage defining means of the invention is in direct engagement with distendable membrane 366 which, after being distended, will tend to return to its less distended configuration. It is to be noted that the shape of the conformable ullage will continuously vary as the distendable membrane distends outwardly from the base during reservoir filling and then tends to return to its less distended configuration during fluid delivery.

While the conformable ullage, or mass 388 is here constructed from a flowable gel, the conformable ullage can also be constructed from a number of materials such as various types of foams, fluids and soft elastomers. In some instances, the conformable ullage may comprise an integral conforming mass. In other instances, such as when a gel or fluid is used as the ullage medium, an encapsulation barrier member such as member 354 must be used to encapsulate the gel or fluid and to provide an appropriate interface to the fluid contained in the reservoir. Alternatively, a separate pliable film can be used to encapsulate the gel or other fluid medium.

Once reservoir 356 is filled with fluid from the container subassembly of the fill assembly, the fluid will remain in the reservoir until such time as an outlet flow path of the fluid delivery assembly is opened. Once this path is opened in a manner presently to be described, distendable membrane 366 will tend to return to its less distended configuration and will act upon the conformable ullage 388 and the barrier member 354 in a manner to cause fluid to flow from reservoir 356 outwardly through flow passageways 360 and 362 and then into chamber 390 via the flow control means 392 (FIG. 35).

Referring once again to FIGS. 31 and 34, it is to be noted that base portion 406 and adapter member 330 include locking means for locking the adapter member 330 within receiving chamber 404 after the fill subassembly has been mated with the fluid delivery device. These locking means are here provided in the form of a series of forwardly and rearwardly disposed locking teeth 420 and 422 respectively formed on adapter 330 and a locking tab 424 formed on base portion 406. As indicated in FIG. 34, these locking teeth are constructed so that they will slide under the flexible locking tab 424, which is provided proximate the entrance of receiving chamber 404, as the adapter subassembly is urged inwardly of receiving chamber 404. However, once the adapter subassembly has reached the fully inserted position shown in FIG. 34 wherein the fluid is transferred to reservoir 356, locking tab 424 will effectively prevent removal of the adapter subassembly from passageway 404. With this novel construction, once reservoir 356 has been filled with the fluid contained in the container subassembly, the adapter subassembly cannot be removed from the fluid delivery device and, therefore, cannot be reused thereby preventing system adulteration.

Also forming an important aspect of the present invention is the provision of viewing means for viewing the volume of fluid contained within chamber 316 of the fluid container subassembly 308. In the form of the invention shown in the drawings, this viewing means takes the form of an elongated viewing window 428 which is provided in housing 330 (FIG. 27). As indicated in FIG. 27, the body portion 308 of the container subassembly is provided with a plurality of longitudinally spaced-apart index lines, or marks 430, which can be viewed through window 428. Index lines 430 provide reference points for observing the volume of fluid remaining within the container subassembly. A protuberance 330a formed on housing 330 in cooperation with channel 406a (FIGS. 31 and 38) functions to provide polarized orientation of the subassembly as it is introduced into receiving chamber 404.

Referring particularly to FIGS. 31, 40, and 41, in the present form of the invention the delivery means for delivering medicinal fluids from reservoir 356 outwardly of the device comprises a tapered outlet cavity 433 which is formed in base 304 and defines outlet chamber 390. Cavity 433 is adapted to receive a quick connect delivery fitting 435 that comprises a part of the delivery means of the invention. Fitting 435 includes a tapered inboard end portion 435a and a body portion 435b. A central bore 437 extends through portions 435a and 435b and communicates at its outboard end with a cannula 450 which also forms a part of the delivery means of the invention for delivering fluids from the device. When fitting 435 is seated within chamber 390, the inboard end of bore 437 communicates with the chamber and with a stub passageway 452 which houses a portion of the flow control means 392.

In order to lock quick connect delivery fitting 435 in the fluid delivery position, locking means shown here as resiliently deformable locking tabs 454 are provided on the body portion of fitting 435. Tabs 454 lockably engage a locking surface 455 provided on cover 407 (FIG. 40). Upon pushing inwardly on fitting 435, tabs 454 will yieldably deform inwardly so that tapered portion 435a of the fitting can be introduced into chamber 390. As the fitting seats within the chamber, the resiliently deformable locking tabs will spring outwardly and engage locking surface 455 in a manner to lockably interconnect the delivery means with the cover 407.

During this fluid step, fluid will flow from reservoir 356 through passageway 360 through the previously identified flow control means and then into outlet cannula 450 (FIG.

35). The flow control means, which further controls the fluid flow characteristics of the device, here comprises an assemblage 392 which is preferably constructed from a plurality of components 392a, 392b, and 392c. Member 392a is a porous member; member 392b is a rate control element; and member 392c is a porous supporting substrate. Member 392a is preferably constructed from a material comprising polysulfone sold by Gelman Sciences under the name and style of "SUPOR". Member 392b is preferably constructed from a porous polycarbonate material available from Corning Costar Corporation or from a material sold by DuPont under the name and style KAPTON which has been laser drilled or machined to provide appropriate flow orifices. Member 392c can be constructed from a porous polypropylene. After flowing through the flow control means, the liquid medicament will flow outwardly of the device via delivery cannula 450.

Figure 37:
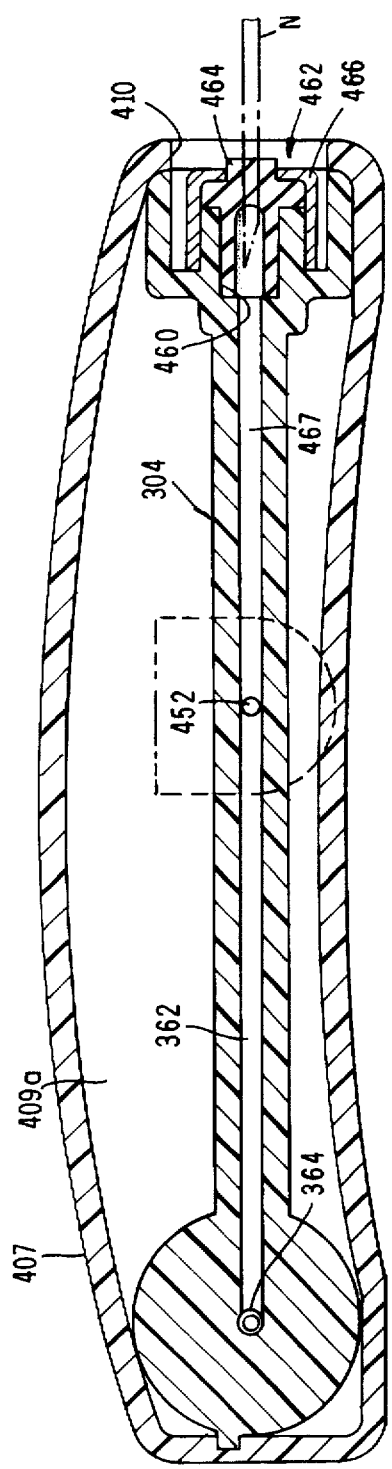
FIG. 37 is an enlarged, cross-sectional view taken along lines 37—37 of FIG. 32.
Figure 36:
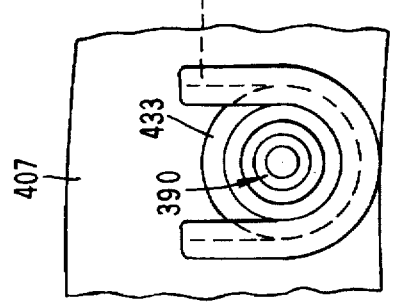
FIG. 36 is a view taken along lines 36—36 of FIG. 35.

An extremely important feature of the apparatus of this latest form of the present invention comprises the previously mentioned bolus injection means which here comprises a bolus injection site mounted in base 304 and accessible through aperture 410 provided in cover 407. Referring particularly to FIGS. 31, 32, and 37, this novel bolus injection means includes a cavity 460 provided in base 304 within which a pierceable septum assembly 462 is mounted. Assembly 462 includes a pierceable septum 464 and a retaining ring 466. Septum 464 is accessible via opening 410 provided in cover 407 and is specially designed to accept a needle "N" of a conventional syringe (see FIG. 37).

Through use of a conventional syringe, a bolus dose can be conveniently introduced into a fluid passageway 467 formed in base 304 via septum 464. The bolus dose will then flow through passage 452 and toward the central bore 437 of quick connect fitting via the flow control means. After passing through the flow control means, the bolus dose will flow into delivery cannula 450.

With the highly novel construction of the device as described in the preceding paragraphs, the patient can continually receive a selected basal dose of liquid medication, such as insulin from reservoir 356. However, should the patient at any time determine that his or her blood sugar level is unduly high, a bolus injection of a predetermined volume can quickly and easily be administered through use of the novel bolus injection means of the invention and in this way appropriately supplement the basal does being delivered from reservoir 356.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid delivery apparatus comprising:
   (a) a fluid delivery assembly having an outlet for delivering fluid from the apparatus, said fluid delivery assembly including:
      (i) a base having a fluid passageway in communication with said outlet;
      (ii) a stored energy means comprising at least one distendable membrane cooperating with said base to define a fluid reservoir in communication with said fluid passageway of said base; and
      (iii) a cover assembly connected to said base, one of said cover assembly and said base having a receiving chamber interconnected with said fluid passageway; and
   (b) a fill assembly interconnected with said fluid delivery assembly for filling said reservoir, said fill assembly comprising:
      (i) a container assembly including:
         a. a container having a fluid chamber; and
         b. means movable within said fluid chamber of said container for urging fluid from said fluid chamber; and
      (ii) an adapter assembly receivable within said receiving chamber for interconnecting said container with said fluid delivery assembly, said adapter assembly comprising a hollow housing for telescopically receiving a part of said container of said container assembly and including a second end;
   (c) delivery means in communication with said fluid reservoir for delivering fluid from said reservoir outwardly of the device; and
   (d) bolus injection means in communication with said delivery means for providing a bolus volume of fluid to said delivery means.

2. An apparatus as defined in claim 1 in which said cover assembly includes a cover connected to said base, said bolus injection means comprising an injection site formed in said base and accessible through said cover assembly.

3. An apparatus as defined in claim 1 including ullage defining means disposed between said base and said cover assembly.

4. An apparatus as defined in claim 3 further including a barrier member disposed between said base and said ullage defining means.

5. An apparatus as defined in claim 1 further including flow control means in communication with said fluid reservoir for controlling fluid flow toward said delivery means.

6. A fluid delivery apparatus comprising:
   (a) a fluid delivery assembly having an outlet for delivering fluid from the apparatus, said fluid delivery assembly including:
      (i) a base having a fluid passageway in communication with said outlet;
      (ii) a stored energy means comprising at least one distendable membrane cooperating with said base to define a fluid reservoir in communication with said fluid passageway of said base; and
      (iii) a cover assembly connected to said base, one of said cover assembly and said base having a receiving chamber interconnected with said fluid passageway; and
   (b) a fill assembly interconnected with said fluid delivery assembly for filling said reservoir, said fill assembly comprising:
      (i) a container assembly including:
         a. a container having a body portion, a fluid chamber, and first and second open ends;
         b. closure means for sealably closing said first end of said container; and
         c. a plunger telescopically movable within said container from a first location proximate said first open end to a second spaced apart location; and
      (ii) an adapter assembly receivable within said receiving chamber, said adapter assembly comprising a hollow housing having a first open end for telescopically receiving a part of said body portion of said container of said container assembly and including a second end;
   (c) delivery means in communication with said fluid reservoir for delivering fluid from said reservoir outwardly of the device; and (d) bolus injection means in communication with said delivery means for providing a bolus volume of fluid to said delivery means.

7. An apparatus as defined in claim 6 in which said cover assembly includes a cover connected to said base, said bolus injection means comprising an injection site formed in said base and accessible through said cover assembly.

8. An apparatus as defined in claim 6, including ullage defining means disposed between said base and said cover assembly.

9. An apparatus as defined in claim 6 further including a barrier member disposed between said base and said ullage defining means.

10. An apparatus as defined in claim 6 further including flow control means in communication with said fluid reservoir for controlling fluid flow toward said delivery means.

11. An apparatus as defined in claim 10 in which said flow control means comprises a rate control element for controlling the rate of fluid flow outwardly of said device.

12. An apparatus as defined in claim 11 in which said delivery means further comprises a quick connect fitting for interconnection with said cover assembly.

13. A fluid delivery apparatus comprising:
  (a) a fluid delivery assembly having an outlet for delivering fluid from the apparatus, said fluid delivery assembly including:
    (i) a base having a fluid passageway in communication with said outlet of the apparatus;
    (ii) a conformable mass overlaying said base for forming in conjunction therewith a reservoir having a fluid port in communication with said fluid passageway;
    (iii) a cover connected to said base, said base having a receiving chamber interconnected with said fluid passageway;
    (iv) a stored energy means for exerting forces on said means defining a conformable ullage, said stored energy means comprising at least one distendable membrane superimposed over said conformable mass, said membrane being distendable by forces imparted thereon by said means defining a conformable ullage in response to fluids introduced into said reservoir, said forces establishing internal stresses within said distendable membrane, said stresses tending to return said distendable membrane toward a less distended configuration; and
    (v) bolus injection means comprising an injection site formed in said base and accessible through said cover for delivering a bolus dose of medication into said outlet;
  (b) a fill assembly interconnected with said fluid delivery assembly for filling said reservoir, said fill assembly comprising:
    (i) a container assembly including:
      a. a container having a body portion, a fluid chamber, and first and second open ends;
      b. closure means for sealably closing said first end of said container; and
      c. a plunger telescopically movable within said container from a first location proximate said first open end to a second spaced apart location; and
    (ii) an adapter assembly receivable within said receiving chamber, said adapter assembly comprising a hollow housing having a first open end for telescopically receiving a part of said body portion of said container of said container assembly and including a second end; and (c) delivery means connected to said outlet of said fluid delivery assembly for delivering fluid from said reservoir outwardly of the device.

14. An apparatus as defined in claim 13 further including a barrier member disposed between said conformable mass and said base.

15. An apparatus as defined in claim 13 in which said conformable mass comprises a gel that is substantially conformable to the continually changing geometry of said distendable membrane as said membrane tends to move toward a less distended configuration.

16. An apparatus as defined in claim 13 in which said delivery means comprises a fluid delivery administration line and a quick connect fitting for interconnecting said administration line with said cover.

17. An apparatus as defined in claim 13 including locking means provided on said cover for locking said adapter assembly within said receiving chamber.

18. An apparatus as defined in claim 13 in which said base has a chamber formed therein and in which said injection site comprises a pierceable septum mounted within said chamber, said chamber being in communication with said fluid passageway.

19. An apparatus as defined in claim 13 further including flow control means in communication with said fluid reservoir for controlling fluid flow toward said delivery means.

20. An apparatus as defined in claim 19 in which said flow control means comprises a rate control element for controlling the rate of fluid flow outwardly of said device.

21. A fluid delivery apparatus comprising:
  (a) a fluid delivery assembly having an outlet for delivering fluid from the apparatus, said fluid delivery assembly including:
    (i) a base having an upper surface, a lower surface, and a fluid passageway formed in said base intermediate said upper and lower surfaces, said fluid passageway being in communication with said outlet of the apparatus and having first and second ends;
    (ii) a conformable gel overlaying said base for forming in conjunction therewith a reservoir having a fluid port in communication with said second end of said passageway formed in said base;
    (iii) a cover connected to said base, said base having a receiving chamber interconnected with said first end of said fluid passageway formed in said base;
    (iv) an elastomeric membrane for exerting forces on said gel, said elastomeric membrane being superimposed over said gel, said membrane being distendable by forces imparted thereon by said gel in response to fluids introduced into said reservoir, said forces establishing internal stresses within said elastomeric membrane, said stresses tending to return said elastomeric membrane toward a less distended configuration;
    (v) bolus injection means comprising an injection site formed in said base for delivering a bolus dose of medication into said outlet; and
    (vi) flow control means in communication with said reservoir for controlling fluid flow toward said outlet;
  (b) a fill assembly interconnected with said fluid delivery assembly for filling said reservoir, said fill assembly comprising:
    (i) a container assembly including:
      a. a container having a body portion, a fluid chamber, and first and second open ends;
      b. closure means for sealably closing said first end of said container; and c. a plunger telescopically movable within said container from a first location proximate said first open end to a second spaced apart location; and (ii) an adapter assembly receivable within said receiving chamber, said adapter assembly comprising a hollow housing having a first open end for telescopically receiving a part of said body portion of said container of said container assembly and including a second end; and (c) delivery means in communication with said reservoir for delivering fluid from said reservoir outwardly of the device.

22. An apparatus as defined in claim 21 in which said base has a chamber formed therein and in which said injection site is mounted within said chamber, said chamber being in communication with said fluid passageway formed in said base.

23. An apparatus as defined in claim 21 further including a barrier member disposed between said base and said gel.

24. An apparatus as defined in claim 21 in which said flow control means comprises a rate control element for controlling the rate of fluid flow toward said outlet of said delivery means.

25. An apparatus as defined in claim 21 further including locking means provided on said cover for locking said adapter assembly within said receiving chamber.

* * * * *